US006838552B1

(12) United States Patent
Mitchell et al.

(10) Patent No.: US 6,838,552 B1
(45) Date of Patent: Jan. 4, 2005

(54) DIAGNOSIS AND MANAGEMENT OF INFECTION CAUSED BY CHLAMYDIA

(75) Inventors: William M. Mitchell, Nashville, TN (US); Charles W. Stratton, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 32 days.

(21) Appl. No.: 09/709,201

(22) Filed: Nov. 8, 2000

Related U.S. Application Data

(63) Continuation of application No. 09/025,521, filed on Feb. 18, 1998, now abandoned, which is a continuation-in-part of application No. 08/911,593, filed on Aug. 14, 1997, now abandoned.

(51) Int. Cl.[7] .................. A61K 51/00; A61K 39/118; A61B 5/055; G01N 33/55; G01N 33/567
(52) U.S. Cl. ............... 530/389.5; 424/1.49; 424/9.34; 424/263.1; 435/7.1; 435/7.2; 435/7.32; 435/7.36; 435/7.8; 435/7.92; 435/7.93; 435/7.94; 435/7.95; 436/512; 436/532; 436/535; 436/545; 436/546; 530/387.1; 530/387.9; 530/388.4
(58) Field of Search ................ 424/263.1; 435/4, 435/7.1, 7.2, 7.36, 7.7, 7.8, 7.9, 7.91, 7.92–7.95, 29, 69.3, 174, 176, 177, 257.6, 331, 340, 344.1; 530/389.5

(56) References Cited

U.S. PATENT DOCUMENTS

| | | | |
|---|---|---|---|
| 5,047,326 A | * | 9/1991 | Pronovost .............. 435/7.36 |
| 5,132,205 A | | 7/1992 | Pronovost et al. ........... 435/5 |
| 5,212,062 A | | 5/1993 | Daniels et al. ............ 435/7.36 |
| 5,236,826 A | | 8/1993 | Marshall .................. 435/7.92 |
| 5,318,892 A | * | 6/1994 | Watanabe et al. ......... 435/7.36 |
| 5,869,608 A | | 2/1999 | Caldwell et al. ............ 530/350 |

FOREIGN PATENT DOCUMENTS

| | | | | |
|---|---|---|---|---|
| EP | 699688 | * | 8/1995 | .......... C07K/16/12 |
| WO | WO 93/19183 | | 9/1993 | |
| WO | WO 98/02546 | | 1/1998 | |

OTHER PUBLICATIONS

Carter et al. 1991. J. of Gen. Micro. 137:465–475.*
Gaydos et al. 1992. Infect. and Immun. 60(12): 5319–5323.*
Melgosa et al. 1991. Infect and Immun. 59(6): 2195–2199.*
Hopp et al., "Prediction of protein antigenic determinants from amino acid sequences," *Proc. Natl. Acad. Sci. USA* 78:3824–3828 (1981).
Van Regenmortel., "Which structural features determine protein antigenicity?," *TIBS* 11:36–39 (1986).

* cited by examiner

*Primary Examiner*—Patricia A. Duffy
*Assistant Examiner*—Ja-Na Hines
(74) *Attorney, Agent, or Firm*—Clark & Elbing LLP

(57) ABSTRACT

The present invention provides a unique approach for the diagnosis and management of infections by Chlamydia species, particularly *C. pneumoniae*. The invention is based, in part, upon the discovery that a combination of agents directed toward the various stages of the chlamydial life cycle is effective in substantially reducing infection. Products comprising combination of antichlamydial agents, novel compositions and pharmaceutical packs are also described.

5 Claims, 4 Drawing Sheets

FIG. 1A

FIG. 1B

Figure 2:
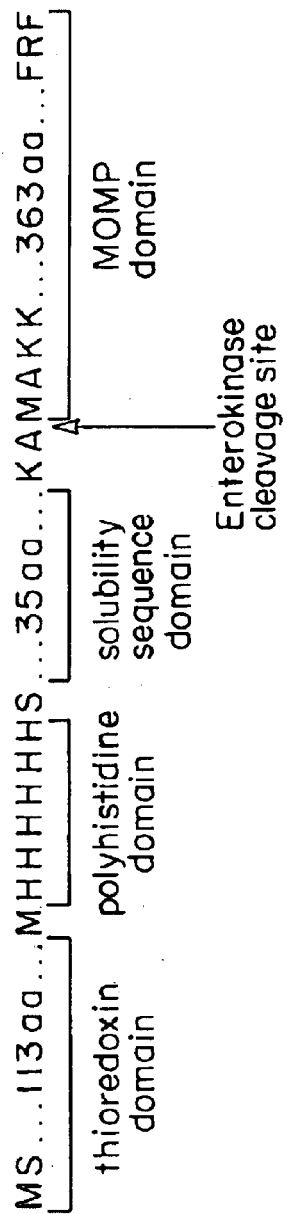

| | | | | | | | | | | | | | | | SEQ ID NO. |
|---|---|---|---|---|---|---|---|---|---|---|---|---|---|---|---|
| CPN90-105 C. pneumoniae | C | T | G | S | A | A | – | A | N | Y | T | T | A | V | D | – | R | P | N | 93 |
| CTP89-105 C. trachomatis (mouse) | C | T | G | D | A | D | L | T | T | A | P | T | P | A | S | – | R | E | N | 94 |
| CTL91-106 C. trachomatis (L2) | C | T | T | A | T | G | N | A | A | A | P | S | T | C | T | A | R | E | N | 95 |
| CPS92-106 C. psitacci | C | A | S | G | T | A | – | S | N | T | T | V | A | A | D

```
                                              SEQ
                                             ID NO.
CPN158-171 C. pneumoniae    C F G V K G T T V N A N E - - - L P   97
CTP158-171 C. trachomatis(mouse)  C F G R D E T A V A A D D - - I P   98
CTL159-175 C. trachomatis(L2)     C F G D N E N H A T V S D S K L V P   99
CPS160-172 C. psitacci      C I G L A G T D F - A N Q - - R P   100
```

FIG. 4

```
                                              SEQ
                                             ID NO.
CPN342-354 C. pneumoniae    C Q I N K F K S R K A C G   101
CTP342-354 C. trachomatis(mouse)  C Q I N K M K S R F A C G   102
CTL342-354 C. trachomatis(L2)     C Q L N K M K S R K A C G   103
CPS342-354 C. psitacci      C Q I N K F K S R F A C G   104
```

FIG. 5

DIAGNOSIS AND MANAGEMENT OF INFECTION CAUSED BY CHLAMYDIA

RELATED APPLICATIONS

This application is a continuation application of U.S. Ser. No. 09/025,521 filed Feb. 18, 1998 now abandoned which is a continuation in part of U.S. Ser. No. 08/911,593 filed Aug. 14, 1997 now abandoned, hereby incorporated by reference.

BACKGROUND OF THE INVENTION

Chlamydiae are obligate intracellular microorganisms which parasitize eukaryotic cells and are ubiquitous throughout the animal kingdom. Members of the chlamydial genus are considered bacteria with a unique biphasic developmental cycle having distinct morphological and functional forms. This developmental growth cycle alternates between 1) intracellular life forms, of which two are currently recognized, a metabolically-active, replicating organism known as the reticulate body (RB) and a persistent, non-replicating organism known as the cryptic phase; and 2) an extracellular life form that is an infectious, metabolically-inactive form known as the elementary body (EB).

EBs are small (300–400 nm) infectious, spore-like forms which are metabolically inactive, non-replicating, and found most often in the acellular milieu. EBs are resistant to a variety of physical insults such as enzyme degradation, sonication and osmotic pressure. This physical stability is thought to be a result of extensive disulfide cross-linking of the cysteine-rich major outer membrane protein (MOMP) (Bavoil et al., *Infection and Immunity*, 44:479–485 (1984); Hackstadt et al., *Journal of Bacteriology*, 161:25–31 (1985); Hatch et al., *Journal of Bacteriology*, 165:379–385 (1986); Peeling et al., *Infection and Immunity*, 57:3338–3344 (1989); J. C. A. Bardwell, *Molecular Microbiology*, 14:199–205 (1994); and T. P. Hatch, *Journal of Bacteriology*, 178:1–5 (1993)). Under oxidizing conditions in the acellular milieu of the host, the outer membrane of EBs is relatively impermeable as well as resistant to inactivation. EBs are thus well suited to survive long enough outside of their hosts to be transmitted to a new host in the form of a droplet nuclei (Theunissen et al., *Applied Environmental Microbiology*, 59:2589–2593 (1993)) or a fomite (Fasley et al., *The Journal of Infectious Diseases*, 168:493–496 (1993))

Infection by members of the genus Chlamydiae induces a significant inflammatory response at the cellular level. For example, genital lesions produced by *Chlamydia trachomatis* frequently elicit a vigorous influx of lymphocytes, macrophages, and plasma cells, suggesting the development of humoral and cellular immunity. Yet, clinically, the initial infection is frequently varied in symptomatology and may even be asymptomatic. Once fully established, the Chlamydia are difficult to eradicate, with frequent relapse following antibiotic therapy. Evidence also indicates that the Chlamydia may become dormant and are then shed in quantities too few to reliably detect by culture.

*Chlamydia pneumoniae* (hereinafter "*C. pneumoniae*") is the most recent addition to the genus Chlamydiae and is isolated from humans and currently is recognized as causing approximately 10 percent of community acquired cases of pneumonia (Grayston et al., *J. Inf. Dis.* 161:618–625 (1990)). This newly recognized pathogen commonly infects the upper and lower respiratory tract and is now recognized as ubiquitous in humans. *C. pneumoniae* is the most recent addition to the genus Chlamydiae and is well-accepted as a human pathogen that may be difficult to eradicate by standard antibiotic therapy (Hammerschlag et al., *Clin. Infect. Dis.* 14:178–182 (1992)). *C. pneumoniae* is known to persists as a silent or mildly symptomatic pathogen, resulting in a chronic, persistent infection (J. Schacter, *In: Baun AL*, eg. *Microbiology of Chlamydia*, Boca Raton, Fla., CRC Press, 1988, pp. 153–165).

The current therapy for suspected/confirmed *C. pneumoniae* infection is with a short course (e.g., 2–3 weeks) of a single antibiotic. *C. pneumoniae* is susceptible in vitro to tetracycline, erythromycin, clarithromycin, and fluoroquinolones such as ofloxacin and sparfloxacin (Kuo et al., *Antimicrob Agents Chemother* 32:257–258 (1988); Welsh et al., *Antimicrob Agents Chemother* 36:291–294 (1992); Chirgwin et al., *Antimicrob Agents Chemother* 33:1634–1635 (1989); Hammerschlag et al., *Antimicrob Agents Chemother* 36:682–683 (1992); Hammerschlag et al., *Antimicrob Agents Chemother* 36:1573–1574); M. R. Hammerschlag, *Antimicrob Agents Chemother* 38:1873–1878 (1994); M. R. Hammerschlag, *Infect. Med.* pp. 64–71 (1994)). Despite this demonstration of in vitro susceptibility, *C. pneumoniae* infections may relapse following antibiotic therapy with these agents. In vitro studies on the persistence of Chlamydiae despite specific and appropriate antibiotic therapy have suggested that the presence of antibiotics promotes the formation of an intracellular, non-replicative state (Beatty et al., *Microbiol. Rev.* 58:686–699 (1994)), typically referred to as the latent or cryptic phase. This change can be thought of as a stringent response and is seen also with nutrient starvation and exposure to γ-interferon. Removal of the stressful influence allows the organism to resume replication. Thus, in this way the organism can escape current antibiotic therapy used in clinical practice.

In view of the chronic and persistent nature of chlamydial infections, there is a need for reliable, accurate methods for diagnosis of pathogenic infection as well as therapeutic approaches to manage the infection. Due to the highly infective nature of Chlamydia EBs and their ability to reinfect cells, there is also a need for antichlamydial therapy which totally eradicates this pathogen, thereby preventing the long term sequelae of such chronic infections.

SUMMARY OF THE INVENTION

The present invention provides a unique approach for the diagnosis and management of infection by Chlamydia species, particularly *C. pneumoniae*. The invention is based upon the discovery that a combination of agents directed toward each of the various stages of the chlamydial life cycle can successfully manage infection and ultimately prevent reinfection/reactivation of the pathogen. Accordingly, one embodiment of the invention pertains to methods of treating infection by a Chlamydia species, comprising administering to an individual in need thereof a combination of anti-chlamydial agents, comprising at least two agents, each of which is effective against a different phase of the chlamydial life cycle. For example, the method can be carried out using agents chosen from among the following groups: a) at least one agent effective against the elementary body phase of the chlamydial life cycle; b) at least one agent effective against the replicating phase of the chlamydial life cycle; and c) at least one agent effective against the cryptic phase of the chlamydial life cycle. The chlamydial pathogen can be eliminated more rapidly when a combination comprising agents directed against each phase of the chlamydial life cycle is administered. For the purposes of this invention, "cryptic phase" embraces any non-replicating, intracellular form, of which there are a number of distinct stages, including but not limited to intracellular EBs, EBs transforming into RBs and vice versa, miniature RBs, non-replicating RBs and the like.

The invention also pertains to novel combinations of antichlamydial agents and to novel pharmaceutical compositions comprising agents at least two antichlamydial agents, each of which is effective against a different phase of the chlamydial life cycle. For example, the agents can be selected from the group consisting of: a) at least one agent effective against the elementary body phase of the chlamydial life cycle; b) at least one agent effective against the replicating phase of the chlamydial life cycle; and c) at least one agent effective against cryptic phase of the chlamydial life cycle. These compositions and combinations of agents can further comprise one or a combination of adjunct compounds, including anti-inflammatory agents, immunosuppressive agents and vitamin C. Use of the combination of antichlamydial agents or compositions thereof for the manufacture of a medicament for the management of Chlamydia infection is also described. In a particular embodiment, the agents can be assembled individually, admixed or instructionally assembled.

The invention also pertains to a novel therapy comprising a specific agent effective against the elementary body phase of the chlamydial life cycle which, if used for a sufficient period of time, allows active infection to be completed without the creation of infectious EBs.

In order to facilitate patient compliance during a course of therapy, the invention provides a means for packaging therapeutic agents, described herein, for the management of Chlamydia infection. For example, a pack can comprise at least two different agents, each of which is effective against a different phase of the chlamydial life cycle. These agents can-be selected from the group consisting of: a) at least one agent effective against the elementary body phase of the chlamydial life cycle; b) at least one agent effective against the replicating phase of the chlamydial life cycle; and c) at least one agent effective against the cryptic phase of the chlamydial life cycle. Optional adjunct compounds, as mentioned previously, can likewise be present in the pack. A preferred pack will comprise a plurality of agents that are directed to at least two, but preferably to all, of the stages of the chlamydial life cycle. The pack can provide unit dosage of the agents or can comprise a plurality of unit dosages, and may be labeled with information, such as the mode and order of administration (e.g., separate, simultaneous or sequential) of each component contained therein.

The invention also encompasses a method for evaluating the infection status of an individual and/or the progress of therapy in an individual undergoing therapy for infection caused by Chlamydia. The method comprises quantifying antibody titer or other measure to the pathogen and comparing the measure to antibody measure quantified at a time earlier in the therapy, whereby the difference between the measures is indicative of the progress of the therapy. The invention also pertains to a method for monitoring the course of therapy for treating infection by Chlamydia, comprising determining presence or absence of Chlamydia in an infected individual at time intervals during course of therapy. In a particular embodiment, this is determined by PCR assay or antigen capture assay for pathogen DNA.

Detection of the presence of Chlamydia in a sample of biological material taken from an individual thought to be infected therewith is important in determining the course of therapy and the agents to be used. This can be achieved by detecting the presence of DNA encoding MOMP of Chlamydia or other chlamydial genes in the individual. In one aspect of the invention, diseases associated with Chlamydia infection, such as inflammatory diseases, autoimmune diseases and diseases in which the individual is immunocompromised, can be treated by managing (e.g., significantly reducing infection or eradicating) the Chlamydia infection using the novel approach described herein. Both clinical and serological improvements/ resolutions in patient status have been demonstrated.

The invention also pertains to a susceptibility test for identifying agent(s) capable of significantly reducing/ eliminating chlamydial infection. The method comprises preparing tissue culture from cell lines; inoculating these cells with Chlamydia in the absence of cycloheximide; allowing the Chlamydia to infect these cells for several days; adding agent(s) to be tested, which agent(s) is/are replaced as needed for the duration of incubation; isolating chlamydial nucleic acid from the cells; and assessing the presence or absence of chlamydial DNA using a suitable nucleotide amplification assay, such as PCR. Preferably the presence or absence of signal for amplified DNA encoding MOMP of Chlamydia or other chlamydial protein is determined. Absence of a signal indicates a reduction in the degree of infection below that which is detectable by nucleic acid amplification techniques and strongly suggests eradication of the microorganism. The susceptability tests described herein are particularly useful as a drug screening tool for assessing the activity of single agents or combinations of agents against Chlamydia infection.

The unique and novel aspect of the susceptabilty test described herewithin is that it measures the presence or absence of chlamydial DNA and thus can detect cryptic forms and/or elementary bodies both of which are infectious, yet are not replicating.

In one embodiment, a suitable nucleotide assay for identifying agents effective against the cryptic form of chlamydia comprises, in the presence of agent(s) to be tested, subjecting cultured cells to protease/reducing agent (e.g., dithiotreitol (DTT)) and protease digestion or guanidine isothiocyanate (also known as guanidine thiocyanate) for a prescribed period of time; extracting DNA from the treated solution; exposing DNA to appropriate polymerase, dNTPs and primers for DNA amplification of MOMP or other protein of the Chlamydia species; and determining the presence or absence of amplified DNA by visualizing the ethidium bromide treated DNA product by gel electrophoresis, for example. In particular embodiments, the Chlamydia species is C. pneumoniae and the appropriate primers are CHLMOMPDB2 and CHLMOMPCB2.

The invention further relates to a method of identifying cells containing the cryptic form of a Chlamydia species by a nucleic acid amplification technique (e.g., PCR) comprising subjecting cultured cells to protease digestion; stopping protease activity; exposing cells to appropriate heat-stable DNA polymerase, dNTPs and labeled primers (e.g., 3'-biotin labeled, 5'-biotin labeled) for amplification of DNA encoding MOMP of the Chlamydia species; washing the cells; exposing the cells to a reporter molecule (e.g., strepavidin-conjugated signal enzyme); exposing the cells to an appropriate substrate for the reporter molecule (e.g., conjugated enzyme); and visualizing the amplified DNA encoding MOMP by visualizing the product of the reaction.

A method of identifying cells containing the cryptic form of Chlamydia comprises treatinq cultured cells, thought to be infected with Chlamydia, with a disulfide reducing agent; subjecting cultured cells to protease digestion; exposing cells to appropriate polymerase, dNTPs and primers for DNA amplification of nucleic acid encoding a chlamydial protein; exposing the cells to a reporter molecule enzyme; exposing the cells to an appropriate substrate for the reporter enzyme; and determining the presence of the cryptic form of Chlamydia by visualizing the amplified DNA encoding a chlamydial protein. Preferably the amplification technique is PCR and the primers are CHLMOMPDB2 and CHLMOMPCB2 of *Chlamydia pneumoniae*.

A similar method can be used as an assay for identifying an agent which is effective against the cryptic form of Chlamydia. Accordingly, the method comprises treating cultured cells grown in the absence of cycloheximide, thought to be infected with Chlamydia, with a disulfide reducing agent; allowing the chlamydia to replicate; adding a test agent; subjecting cultured cells to protease digestion; exposing cells to appropriate polymerase, dNTPs and primers for DNA amplification of a chlamydial protein; exposing the cells to a reporter molecule enzyme; exposing the cells to an appropriate substrate for the reporter enzyme; and determining the presence of cryptic form of Chlamydia by visualizing the amplified DNA encoding a chlamydial protein, such as MOMP.

Also described is a method of detecting chlamydial elementary bodies in a sample comprising contacting the sample with a disulfide reducing agent before using a DNA amplification technique to detect chlamydial DNA in the sample.

The present invention pertains to methods for clearing biological material infected with Chlamydia to produce Chlamydia-free cell lines and animals, and to methods of maintaining biological material, e.g, cell lines and animals, such that they remain Chlamydia-free. According to the method, a biological material is cleared from Chlamydia infection by contacting the biological material with at least two agents, each of which is effective against a different phase of the chlamydial life cycle, until the biological material no longer tests positive for Chlamydia. The agents can be selected from the group consisting of a) agents effective against the cryptic phase of the chlamydial life cycle; b) agents effective against the elementary body phase of the chlamydial life cycle; and c) agents effective against the replicating phase of the chlamydial life cycle. In one embodiment, the agent effective against the elementary body phase is a disulfide reducing agent. In another embodiment, the agent effective against the cryptic phase is a nitroaromatic compound, such as nitroimidazoles, nitrofluans, analogs, derivatives and combinations thereof.

Biological material that has been cleared of Chlamydia infection, according to the methods of this invention, are also described. The biological material can be a continuous cell line such as HeLa-CF, HL-CF, H-292-CF, HuEVEC-CP and McCoy-CF; wherein "CF" is a shorthand annotation for "Chlamydia-free". Alternatively, the biological material can be an animal, such as a mouse, rabbit or other animal model, which is negative for Chlamydia.

The invention also pertains to methods of maintaining a Chlamydia-free status in animals and cell lines which have been cleared of Chlamydia infection by the methods of this invention, or have never been infected, such as their Chlamydia-free offspring or progeny. Cells or animals can be maintained as Chlamydia-free by maintaining them on antibiotics and/or treating their nutrients and environment to ensure that they are Chlamydia-free. Particularly, a source of nutrients to be administered to Chlamydia-free cells or animals can be treated to inactivate or remove any chlamydial elementary bodies therefrom. This can be accomplished by exposing the nutrients to gamma irradiation for a period of time and level of exposure adequate to inactivate the elementary bodies. In addition to, or alternatively, a source of nutrients can be passed through a filtration system to physically remove the chlamydial elementary bodies therefrom. Optionally, the source of nutrients can be first treated with a disulfide reducing agent, such as dithiothreitol, before the filtration step is performed. The filter should be of adequate size such that objects larger than 0.5 microns are prevented from passing through.

The invention further pertains to a diagnostic kit or pack comprising an assembly of materials selected from the group consisting of antibiotics, reagents, Chlamydia-free cell lines, and combinations thereof, or other materials that would be necessary to perform any of the methods described herein.

The invention further relates to a method of detecting viable Chlamydia in a biological material suspected of being contaminated therewith, comprising culturing Chlamydia-free cells or animals in the presence of biological material and then determining the presence or absence of viable Chlamydia in the culture.

BRIEF DESCRIPTION OF THE DRAWINGS

Figure 1A:
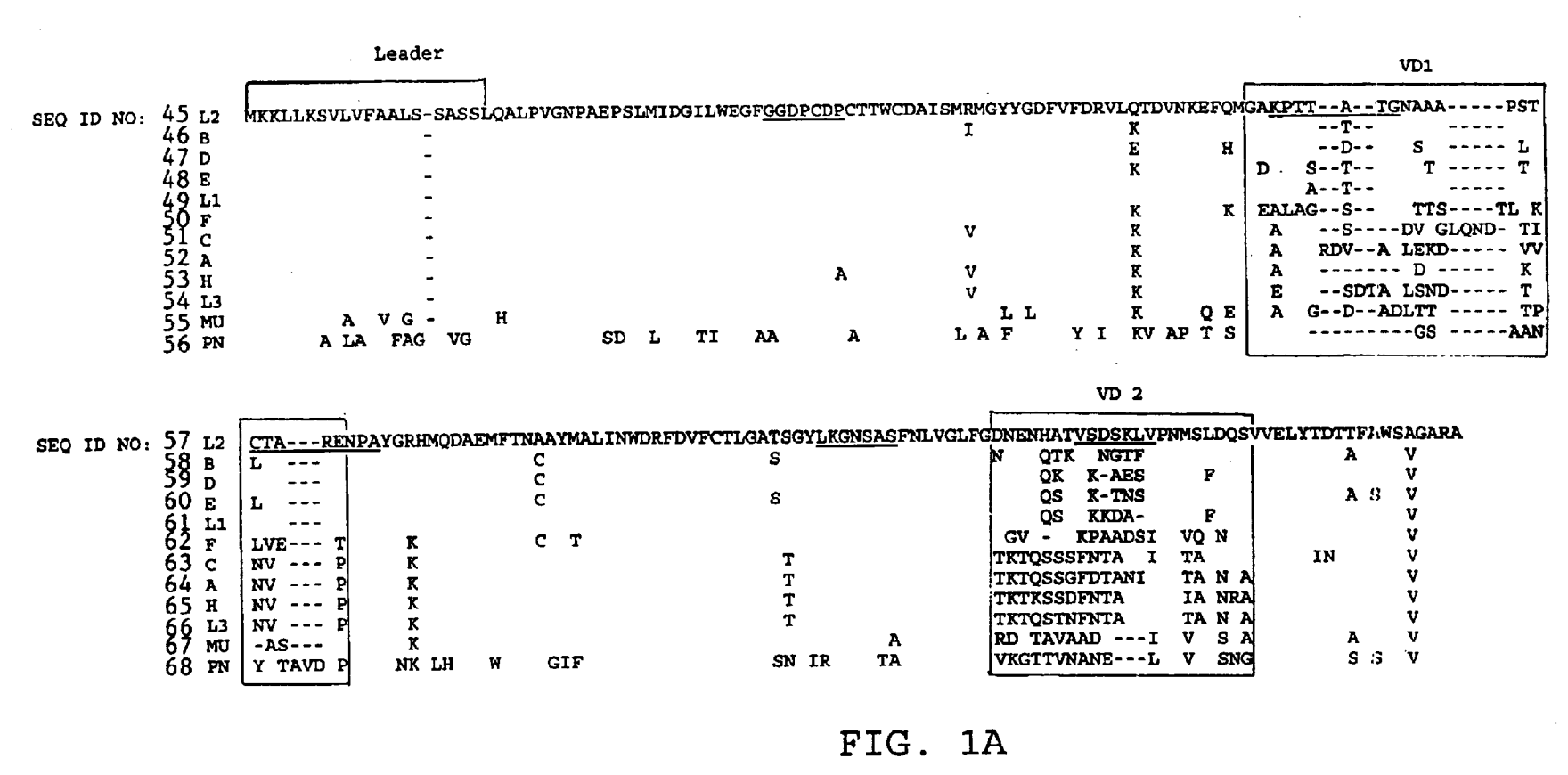

FIGS. 1A and 1B show a sequence alignment of various Chlamydia MOMPs.

FIG. 2 shows the expressed thioredoxin fusion protein containing a polyhistidine affinity chromatography site, an enterokinase cleavage site, and the full length MOMP protein with an alanine insertion after aal. Amino to carboxyl reads left to right. Total amino acid content in the expressed protein is 530 residues.

FIG. 3 illustrates the constant and variable domain (VD) of various Chlamydia species.

FIG. 4 illustrates the peptide amino acid sequences employed for the construction of peptide based ELISAs with species specificity for VD1.

FIG. 5 illustrates the peptides for VD2 which are used similarly to the VD1 sequences.

DETAILED DESCRIPTION OF THE INVENTION

This invention describes specific antichlamydial agents that are used singly or in combination to eliminate or interfere with more than one of the distinct phases of the life cycle of Chlamydia species. These chlamydial phases include the intracellular metabolizing/replicating phase; the intracellular cryptic phase; and the extracellular EB phase. Current concepts of susceptibility testing for chlamydiae and antimicrobial therapy for their associated infections address only one phase, the replicating phase. Unless multiple phases of the life cycle are addressed by antichlamydial therapy, the pathogen is likely to escape the desired effects of the antimicrobial agent(s) used and cause recurrent infection after reactivation from latency.

Diagnostic and therapeutic methods for the management of Chlamydia infections are described in detail below. For the purposes of this invention, "management of Chlamydia infection" is defined as a substantial reduction in the presence of all phases/forms of Chlamydia in the infected host by treating the host in such a way as to minimize the sequellae of the infection. Chlamydia infections can thus be managed by a unique approach referred to herein as "combination therapy" which is defined for the purpose of this application as the administration of multiple agents which together are directed at least two but preferably each of the multiple phases of the chlamydial life cycle, each agent taken separately, simultaneously or sequentially over the course of therapy. When used alone, these agents are unable to eliminate chlamydial infection. The diagnostic methods and combination therapies described below are generally applicable for infection caused by any Chlamydia species, such as C. pneumoniae, C. trachomatis, C. psittaci and C. pecorum. Infections in which the causative agent is C. pneumoniae are emphasized.

Antichlamydial agents, which have been identified as effective against Chlamydia by the susceptibility testing methods described herein, can be used singly or in combination to manage Chlamydia infection. For example, compounds identified as anti-cryptic phase drugs, anti-EB phase drugs, anti-DNA-dependent RNA polymerase drugs and nicotinic acid cogener drugs can be used alone or in combination to eliminate, reduce or prevent one or more of the distinct phases of the chlamydial life cycle. These compounds have not heretofore been shown to have antichlamydial activity.

Diagnosis of Chlamydia Infection

The invention pertains to methods for diagnosing the presence of Chlamydia in a biological material, as well as to the use of these methods to evaluate the serological status of an individual undergoing antichlamydial combination therapy. For purposes of this application, "biological material" includes, but is not limited to, bodily secretions, bodily fluids and tissue specimens. Examples of bodily secretions include cervical secretions, trachial-bronchial secretions and pharyngeal secretions. bodily fluids include blood, sweat, tears, cerebral spinal system fluid, serum, urine, snyovial fluid and saliva. Animals, cells and tissue specimens such as from a variety of biopsies are embraced by this term.

In one embodiment, peptide-based assays are disclosed for the detection of one or more immunoglobulins, such as IgG, IgM, IgA and IgE, against antigenic determinants within the full length recombinant MOMPs of various Chlamydia species. Detection of IgG and/or IgM against antigenic determinants within the the full length recombinant MOMP of C. pneumoniae is preferred. IgA determinations are useful in the analysis of humoral responses to Chlamydia in secretions from mucosal surfaces (e.g., lung, GI tract, gerontourinary tract, etc.). Similarly, IgG determinations are useful in the analysis of allergic manifestatins of disease. Table 1 below provides the GenBank Accession numbers of various MOMPs for Chlamydia species.

TABLE 1

| Species | Strain | ID | GenBank Accession No. |
|---|---|---|---|
| C. trachomatis | A | CTL/A | M33636 |
| C. trachomatis | A | CTL/A | M58938 M33535 |
| C. trachomatis | A | CTL/A | J03813 |
| C. trachomatis | B | CTL/B | M33636 |
| C. trachomatis | C | CTL/L | M17343 M19128 |
| C. trachomatis | D | CTL/D | A27838 |
| C. trachomatis | E | CTL/E | X52557 |
| C. trachomatis | F | CTL/F | X52080 M30501 |
| C. trachomatis | H | CTL/H | X16007 |
| C. trachomatis | L1 | CTL/L1 | M36533 |
| C. trachomatis | L2 | CTL/L2 | M14738 M19126 |
| C. trachomatis | L3 | CTL/L3 | X55700 |

TABLE 1-continued

| Species | Strain | ID | GenBank Accession No. |
|---|---|---|---|
| C. trachomatis | Mouse Pneumo | CTL/MP | X60678 |
| C. pecorum | Ovine Polyarthritis | CPC/OP | Z18756 |
| C. psittaci | Strain 6BC | CPS/6B | X56980 |
| C. psittaci | Feline | CPS/F | X61096 |
| C. trachomatis | Da | CTL/DA | X62921 S45921 |
| C. pneumoniae | TWAR | CPN/HU1 | M64064 M34922 M64063 |
| C. pneumoniae (? C. pecorum) | Horse | CPN/EQ2 | L04982 |
| C. pneumoniae | TWAR | CPN/MS | not assigned |
| C. psittaci | Horse | CPS/EQ1 | L04982 |

For example, a biological material, such as a sample of tissue and/or fluid, can be obtained from an individual and a suitable assay can be used to assess the presence or amount of chlamydial nucleic acids or proteins encoded thereby. Suitable assays include immunological methods such as enzyme-linked immunosorbent assays (ELISA), including luminescence assays (e.g., fluorescence and chemiluminescence), radioimmunoassay, and immunohistology. Generally, a sample and antibody are combined under conditions suitable for the formation of an antibody-protein complex and the formation of antibody-protein complex is assessed (directly or indirectly). In all of the diagnostic methods described herein, the antibodies can be directly labeled with an enzyme, fluorophore, radioisotope or luminescer. Alternatively, antibodies can be covalently linked with a specific scavenger such as biotin. Subsequent detection is by binding avidin or strepavidin labeled with an indicator enzyme, flurophore, radioisotope, or luminescer. In this regard, the step of detection would be by enzyme reaction, fluorescence, radioactivity or luminescence emission, respectively.

The antibody can be a polyclonal or monoclonal antibody, such as anti-human monoclonal IgG or anti-human monoclonal IgM. Examples of useful antibodies include mouse anti-human monoclonal IgG that is not cross reactive to other immunoglobulins (Pharmagen; Clone G18–145, Catalog No. 34162D); mouse anti-human monoclonal IgM with no cross reactivity to other immunoglobulins (Pharmagen; Clone G20–127, catalog No. 34152D). Peptide-based immunoassays can be developed which are Chlamydia specific or provide species specificity, but not necessarily strain specificity within a species, using monoclonal or polyclonal antibodies that are not cross-reactive to antigenic determinants on MOMP of a chlamydial species not of interest.

Recombinant-based immunological assays have been developed to quantitate the presence of immunoglobulins against the Chlamydia species. Full length recombinant Chlamydia MOMP can be synthesized using an appropriate expression system, such as in E. coli or Baculovirus. The expressed protein thus serves as the antigen for suitable immunological methods, as discussed above. Protein-based immunological techniques can be designed that are species- and strain-specific for various Chlamydia.

Diagnosis of chlamydial infection can now be made with an improved IgM/IgG C. pneumoniae method of quantitation using ELISA techniques, Western blot confirmation of ELISA specificity and the detection of the MOMP gene of C. pneumoniae in serum using specific amplification primers that allow isolation of the entire gene for analysis of expected strain-specific differences.

Any known techniques for nucleic acid (e.g., DNA and RNA) amplification can be used with the assays described herein. Preferred amplification techniques are the polymerase chain reaction (PCR) methodologies which comprise solution PCR and in situ PCR, to detect the presence or absence of unique genes of Chlamydia. Species-specific assays for detecting Chlamydia can be designed based upon the primers selected. Examples of suitable PCR amplification primers are illustrated below in Table 2. Examples of preferred primers are illustrated in Table 3.

TABLE 2

Initial and Terminal Nucleotide Sequences of Chlamydial MOMP Genes
in which entire sequence is known

| GenBank Accession No. | ID | Initial Fifty Nucleotides | SEQ ID NO. |
|---|---|---|---|
| M64064/M34922/M64063 | CPNHU1 | ATGAAAAAAACTCTTAAAGTCGGCGTTATTATCCGCCGCATTTGCTGGTTC | 1 |
| None | CPNHU2[a] | ATGAAAAAAACTCTTAAAGTCGGCGTTATTATCCGCCGCATTTGCTGGTTC | 2 |
| L04982 | CPNEQ1 | ATGAAAAAAACTCTTGAAGTCGGCATTATTGTTTGCCGCTACGGGTTCCGC | 3 |
| L04982 | CPNEQ2 | ATGAAAAAAACTCTTAAAGTCGGCGTTATTATCCGCCGCATTTGCTGGTTC | 4 |
| X56980 | CPS/6B | ATGAAAAAAACTCTTGAAATCGGCATTATTGTTTGCCGCTACGGGTTCCGC | 5 |
| N36703 | CPS/AB1 | ATGAAAAAAACTCTTGAAATCGGCATTATTGTTTGCCGCTACGGGTTCCGC | 6 |
| L39020 | CPS/AB2 | ATGAAAAAAACTCTTGAAATCGGCATTATTGTTTGCCGCTACGGGTTCCGC | 7 |
| L25436 | CPS/AV/C | ATGAAAAAAACTCTTGAAATCGGCATTATTATTTGCCGCTACGGGTTCCGC | 8 |
| XE61096 | CPS/F | ATGAAAAAAACTCTTAAAATCGGCATTATTATTTGCCGCTGCGGGTTCCGC | 9 |
| M33636/N58938/J03813 | CTL/A | ATGAAAAAAACTCTTGAAATCGGTATTAGTATTTGCCGCTTTGAGTTCTGC | 10 |
| M17343/M19128 | CTL/C | ATGAAAAAAACTCTTGAAATCGGTATTAGTATTTGCCGCTTTGAGTTCTGC | 11 |
| X62921/S45921 | CTL/DA | ATGAAAAAAACTCTTGAAATCGGTATTAGTATTTGCCGCTTTGAGTTCTGC | 12 |
| X52557 | CTL/E | ATGAAAAAAACTCTTGAAATCGGTATTAGTATTTGCCGCTTTGAGTTCTGC | 13 |
| X52080/M30501 | CTL/F | ATGAAAAAAACTCTTGAAATCGGTATTAGTATTTGCCGCTTTGAGTTCTGC | 14 |
| X16007 | CTL/H | ATGAAAAAAACTCTTGAAATCGGTATTAGTATTTGCCGCTTTGAGTTCTGC | 15 |
| M36533 | CTL/L1 | ATGAAAAAAACTCTTGAAATCGGTATTAGTGTTTGCCGCTTTGAGTTCTGC | 16 |
| M14738/M19126 | CTL/L2 | ATGAAAAAAACTCTTGAAATCGGTATTAGTGTTTGCCGCTTTGAGTTCTGC | 17 |
| X55700 | CTL/L3 | ATGAAAAAAACTCTTGAAATCGGTATTAGTGTTTGCCGCTTTGAGTTCTGC | 18 |
| X60678 | CTL/MP | ATGAAAAAAACTCTTGAAATCGGTATTAGCATTTGCCGTTTTGGGTTCTGC | 19 |

| Chlamydial Species | Strain | ID | Terminal Fifty Nucleotides | SEQ ID NO. |
|---|---|---|---|---|
| C. pneumoniae | TWAR | CPNHU1 | GTTTAATTAACGAGAGAGCTGCTCACGTATCTGGTCAGTTCAGATTCTAA | 20 |
| C. pneumoniae | MS | CPNHU2 | GTTTAATTAACGAGAGAGCTGCTCACGTATCTGGTCAGTTCAGATTCTAA | 21 |
| C. psittaci | Horse | CPNEQ1 | CAACGTTAATCGACGCTGACAAATGGTCAATCACTGGTGAAGCACGCTTA | 22 |
| C. pneumoniae | Horse | CPNEQ2 | CTTTAATTAACGAGAGAGCTGCTCACATATCTGGTCAGTTCAGATTCTAA | 23 |
| C. psittaci | SBE | CPS/6B | AACGTTAATCGACGCTGACAAATGGTCAATCACTGGTGAAGCACGCTTAA | 24 |
| C. peittaci | Ewe abortion | CPS/AB1 | AACGTTAATCGACGCTGACAAATGGTCAATCACTGGTGAAGCACGCTTAA | 25 |
| C. peittaci | Bovine abortion | CPS/AB2 | GCTTAATCAATGAAAGAGCCGCTCACATGAATGCTCAATTCAGATTCTAA | 26 |
| C. peittaci | Avian | CPS/AV/C | GCTTAATCAATGAAAGAGCTGCTCACATGAATGCTCAATTCAGATTCTAA | 27 |
| C. peittaci | Feline | CPS/F | GCTTAATCGACGAAAGAGCTGCTCACATTAATGCTCAATTCAGATTCTAA | 28 |
| C. trachomatis | Hu/A | CTL/A | CGCAGTTACAGTTGAGACTCGCTTGATCGATGAGAGAGCAGCTCACGTAA | 29 |
| C. trachomatis | Hu/C | CTL/C | GCTTGATCGATGAGAGAGCAGGTCACGTAAATGCACAATTCCGGTTCTAA | 30 |
| C. trachomatis | Hu/Da | CTL/DA | GCTTGATCGATGAGAGAGCAGCTCACGTAAATGCACAATTCCGCTTCTAA | 31 |
| C. trachomatis | Hu/E | CTL/E | CGCTTGATCGATGAGAGACTGCTCACGTAAATGCACAATTCCGCTTCTAA | 32 |
| C. trachomatis | Hu/F | CTL/F | GCTTGATCGATGAGAGAGCTGCTCACGTAAATGCACAATTCCGCTTCTAA | 33 |
| C. trachomatis | Hu/H | CTL/H | GCTTGATCGATGAGAGAGCAGCTCACGTAAATGCACAATTCCGCTTCTAA | 34 |
| C. trachomatis | Hu/L1 | CTL/L1 | GCTTGATCGATGAGAGAGCTGCTCACGTAAATGCACAATTCCGCTTCTAA | 35 |
| C. trachomatis | Hu/L2 | CTL/L2 | GCTTGATCGATGAGAGAGCTGCTCACGTAAATGCACAATTCCGCTTCTAA | 36 |
| C. trachomatis | Hu/L3 | CTL/L3 | GCTTGATCGATGAGAGAGCAGCTCACGTAAATGCACAATTCCGCTTCTAA | 37 |
| C. trachomatis | Mouse | CTL/MP | GCTTGATCGATGAAAGAGCAGCTCACGTAAATGCTCAGTTCCGTTTCTAA | 38 |

[a]Sequence from a cerebral spinal fluid of a patient with multiple sclerosis isolated by the inventors. Sequence is identical to TWAR C. pneumoniae with exception of a C/T mutation at NT 54 and a G/A mutation at NT 126.
[b]Terminator condon underlined

TABLE 3

Primers for PCR Amplification of Entire MOMP Gene[a]

| Chlamydia | | | | | |
|---|---|---|---|---|---|
| Species | Strain | ID | Sequence | $T_m$[b] | SEQ ID NO. |
| | | | Plus Strand Primer | | |
| C. pneumoniae | TWAR | CHLMOMPDB2 | ATGAAAAAAC TCTTAAAGTC GGCGTTATTA TCCGCCGC | 61.4° | 105 |
| C. trachomatis | L2 | CTMOMPL2DB | ATGAAAAAAC TCTTGAAATC GGTATTAGTG TTTGCCGCTT TGAG | 61.2° | 106 |
| C. psittaci | Feline | PSOMPFPN-D | ATGAAAAAAC TCTTAAAATC GGCATTATTA TTTGCCGCTG CGGG | 62.1° | 107 |

TABLE 3-continued

| Primers for PCR Amplification of Entire MOMP Gene[a] | | | | | |
|---|---|---|---|---|---|
| Chlamydia | | | | | SEQ |
| Species | Strain | ID | Sequence | $T_m$[b] | ID NO. |
| *C. psittaci* | 6BC | PSOMP 6BC-b | ATGAAAAAAC TCTTGAAATC GGCATTATTG TTTGCCGCTA CGGG | 63.0° | 108 |
| *C. trachomatis* | Mouse | CTMU MOMP-D | ATGAAAAAAC TCTTGAAATC GGTATTAGCA TTTGCCGTTT TGGGTTCTGC | 63.5° | 109 |
| | | | Minus Strand Primer | | |
| *C. pneumoniae* | TWAR | CHLMOMP CB2 | TTAGAATCTG AACTGACCAG ATACGTGAGC AGCTCTCTCG | 64.4° | 110 |
| *C. trachomatis* | L2 | CTMOMP L2CB | TTAGAAGCGG AATTGTGCAT TTACGTGAGC AGCTC | 61.5° | 111 |
| *C. psittaci* | Feline | PSOMP FPN_C | TTAGAATCTG AATTGAGCAT TAATGTGAGC AGCTCTTTCG TCG | 62.2° | 112 |
| *C. psittaci* | 6BC | PSOMP GBC_C | TTAGAATCTG AATTGACCAT TCATGTGAGC AGCTCTTTCA TTGATTAAGC G | 63.4° | 113 |
| *C. trachomatis* | Mouse | CTMU MOMP_C | TTAGAAACGG AACTGAGCAT TTACGTGAGC TGCTCTTTCA TC | 63.2° | 114 |

[a]All primers amplify under identical amplification conditions: 94° C. for 1 min., 58° C. for 2 min., 74° C. for 3 min., for 35 cycles with 72° C. for 10 min. extension of last cycle.
[b]Melting temperature in degrees Celsius of a nucleic acid isomer based on the equation of Mermur and Doty (J. Mol. Biol. 5: 109–118, 1962) where $T_m = 81.5 + 16.6 \log_{10} (Na^+/K^+) + 41 (GC) - 600/L$ where $(Na^+/K^+)$ in the molar cation concentration, GC in the mole fraction of GC and L is the sequence fragment length. $(Na^+/K^+)$ used for computation was 0.05 M.

Ligase chain reaction can also be carried out by the methods of this invention; primers/probes therefor can be constructed using ordinary skill. Amplification of the entire MOMP gene is useful for mutational analysis and the production of recombinant MOMP. Shorter primers can be used for specific amplification of most of the MOMP genome with a modification of amplification protocol. For example, a 22 bp negative strand primer of the sequence 5'-CAGATACGTG AGCAGCTCTC TC-3' (CPNMOMPC; SEQ ID NO. 39) with a computed $T_m$=55° plus a 25bp positive strand primer of the sequence 5'-CTCTTAAAGT CGGCGTTATT ATCCG-3' (CPNMOMPD; SEQ ID NO. 40) with a computed $T_m$=53.9° can be used as a primer pair by adjusting the hybridization step in the amplification protocol (Table 2) from 58° C. to 50° C. Similarly, smaller regions of MOMP can be amplified by a large variety of primer pairs for diagnostic purposes although the utility of strain identification is reduced and amplification may be blocked if one or both primer pairs hybridize to a region that has been mutated. Extensive experience with the full length MOMP PCR amplification indicates that mutational events within the CHLMOMPD32 and CHLMOMPCB2 hybridization sites are rare or non-existent.

The nucleic acid amplification techniques described above can be used to evaluate the course of antichlamydial therapy. The continued absence of detectable chlamydial DNA encoding MOMP as a function of antichlamydial therapy is indicative of clinical management of the chlamydial infection. Serological improvement can be based upon the current serological criteria for eradication of chronic Chlamydia reported below in Table 4.

TABLE 4

| Serological Criteria for Eradication of Chronic *Chlamydia pneumoniae* Infection | |
|---|---|
| IgM | ≦1:25 |
| IgG | Stable titer 1:100 |
| PCR | Negative |

Preferred PCR techniques are discussed in detail below in the Example Section. In general, solution PCR is carried out on a biological material by first pre-incubating the material in an appropriate reducing agent that is capable of reducing the disulfide bonds which maintain the integrity of the MOMP and other surface proteins of the chlamydial elementary bodies, thereby compromising the outer protective shell of the EBs and allowing protease penetration. Suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. Appropriate concentrations of these reducing agents can be readily determined by the skilled artisan without undue experimentation using a 10 μM concentration of dithiothreitol (the preferred reducing agent) as a guideline. Failure to include a reducing agent in the initial step may prevent DNA of EBs from being isolated in the subsequent step. Data presented in Example 1 shows the effects of various reducing agents on the susceptibility of EBs to proteinase K digestion. The in vitro data shows that dithiothreitol is most effective at opening EBs for protease digestion.

Once the outer shell of the EBs has been released, the pre-incubated material is subjected to protein digestion using a protease (e.g., proteinase K), or functionally equivalent enzyme. The DNA is extracted and subjected to a nucleic acid amplification technique, e.g., PCR. The entire gene or portion thereof containing unique antigenic determinant(s) encoding MOMP or other suitable gene can then be amplified using appropriate primers flanking the gene to be amplified. For example, the gene or portion thereof can be the gene encoding MOMP, OMP-B, GRO-ES, GRO-EL, DNAK, 16S RNA, 23S RNA, the gene encoding ribonuclease-P 76 kd attachment protein or a KDO-transferase gene. In an alternative method, guanidine thiocyanate, at preferably a concentration of 4M, or functionally equivalent reducing denaturant may be substituted for the disulfide reduction/protease steps.

Figure 1B:
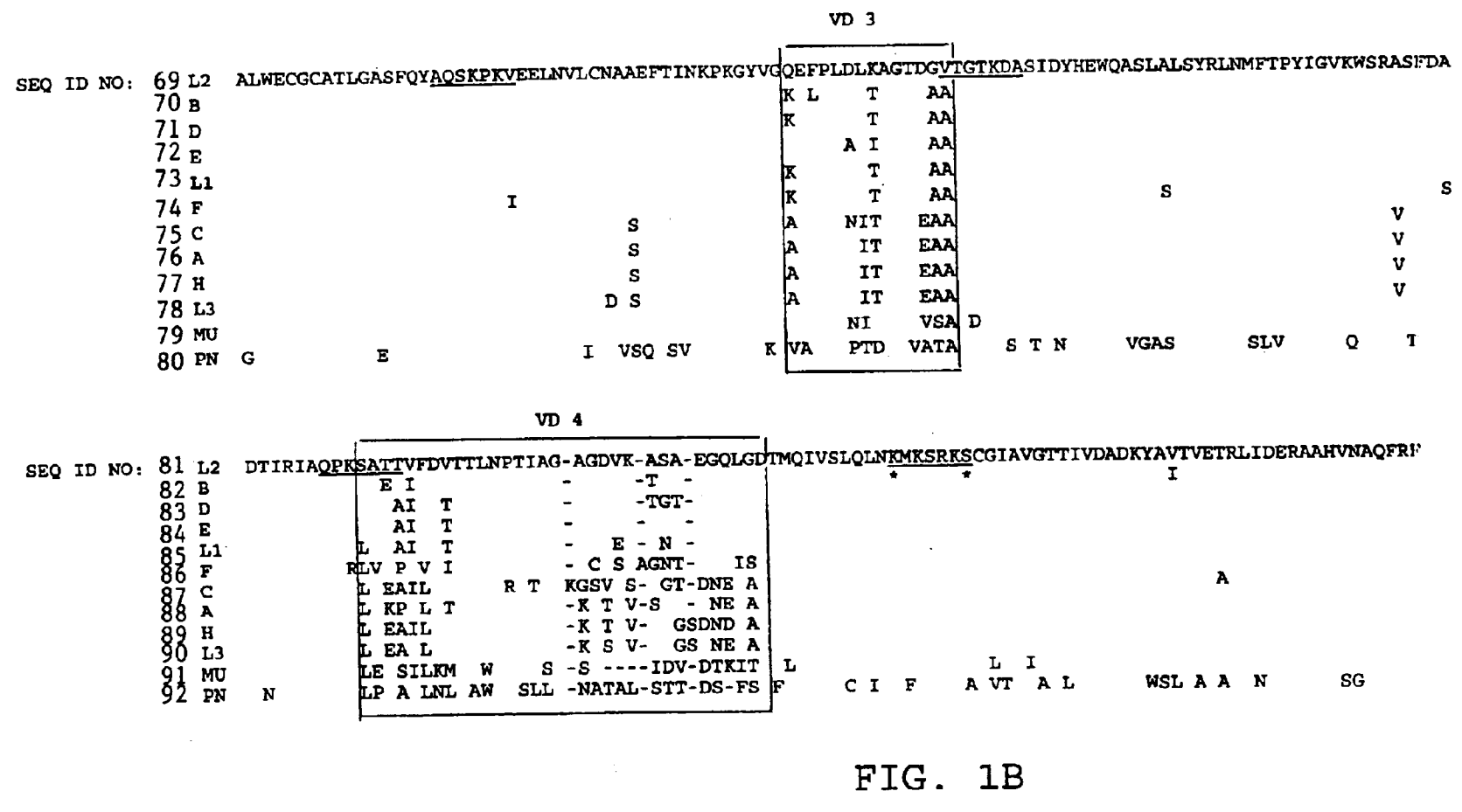

The amplified DNA is then separated and identified by standard electrophoretic techniques. DNA bands are identified using ethidium bromide staining and UV light detection. PCR primers can be designed to selectively amplify DNA encoding MOMP of a particular Chlamydia species, such as the MOMP of *C. pneumoniae, C. pecorum, C. trachomatis, C. psittaci* (See FIG. 1). Primers that are from about 15-mer to about 40-mer can be designed for this purpose.

For in situ PCR, the amplification primers are designed with a reporter molecule conjugated to the 5'-terminus. Suitable reporter molecules are well known and can be used herein. However, biotin-labeled primers are preferred. For the MOMP gene, the primers CHLMOMPDB2 and CHL-MOMPCB2 have been engineered with a biotin at the 5'-terminus. For in situ PCR, using biotin labels incorporated at the 5'-terminus of the amplification primers, each DNA chain amplification results in each double strand DNA containing 2 molecules of biotin. Alternatively, other specific DNA sequences can be used, although the above-described sequence is the preferred embodiment since the large product produced (1.2 kb) prevents diffusion that may be encountered with smaller DNA amplifications. Similarly, other detection labels can be incorporated (i.e., fluorescein, for example) at the 5'-end or digoxigenin-dUTP (replacement for dTPP) can be incorporated within the amplified DNA. Alternatively to labeling the product, specific hybridization probes to constant regions of the amplified DNA can be used to identify an amplified product. This latter method has particular utility for the construction of automated laboratory equipment for solution-based PCR. For example, strepavidin-coated ELISA plates can be used to capture one or both strands of a biotin 5'-labeled DNA with detection by fluorescence of a fluorescein or other incorporated fluorophore detection probe.

Clearing and Maintaining Chlamydia-free Organisms

The present invention provides a unique approach for creating and maintaining animals and cell lines which are free of Chlamydia infection. Also described herein are methods for creating nutrients and culture media that are suitable for use with animals and cell lines that have been cleared of Chlamydia infection.

Attempts to culture isolates of *C. pneumoniae* from blood and cerebrospinal fluid (CSF) have resulted in the discovery that the continuous cell lines routinely used to cultivate *C. pneumoniae* are cryptically infected with *C. pneumoniae*. These include not only in house stocks of HeLa, HL, H-292, HuEVEC and McCoy cells, but also stocks obtained from the American Type Culture Collection (ATCC), The University of Washington Research Foundation for HL cells, as well as a commercial supplier (Bartells) of H-292 and McCoy cells for the clinical culture of Chlamydia. The presence of a cryptic form of *C. pneumoniae* in these cells has been repeatedly demonstrated by solution PCR amplifying the MOMP. In situ PCR in HeLa cells against the MOMP demonstrates the MOMP genes to be present in 100% of cells. Nevertheless, fluoroscenated mAb to LPS in McCoy cells does not yield any indication of Chlamydia (i.e., reactive against all Chlamydia) while fluoroscenated mAb to *C. pneumaniae* MOMP yields a generalized fluorescence throughout the cytoplasm that can be confused with non-specific autofluorescence. Infection with *Chlamydia trachomatis* (Bartells supply) yields the typical inclusion body staining with the LPS mAb (i.e., cross reactive with all species of Chlamydia) with no change in cytoplasmic signal with anti-MOMP mAb against *C. pneumoniae*. These findings (solution PCR, in situ PCR, mAb reactivity) were interpreted as consistent with a cryptic (non-replicating) infection by *C. pneumoniae* of cells commonly used to culture the organism. Further, virtually all rabbits and mice tested to date have PCR signals for the *C. pneumoniae* MOMP gene.

This creates a currently unrecognized problem of major significance for those clinical labs providing *C. pneumoniae* culture services as well as investigators who now do not know whether their results in animals or in cell culture will be affected by cryptic chlamydial contamination. Clinical and research laboratories currently have no way to determine whether an organism is, in fact, Chlamydia-free.

This invention pertains to a method for clearing cells and animals of *C. pneumoniae* and keeping them clear. Clearing them entails contacting the infected organism with agents used singly or in combination to eliminate or interfere with more than one of the distinct phases of the life cycle of Chlamydia species. Keeping them clear entails either maintaining them on antibiotics and/or treating their nutrients and environment to ensure they are Chlamydia-free. In a preferred embodiment, maintenance conditions comprise a combination of isoniazid (INH) (1 μg/ml), metronidazole (1 μg/ml), and dithiothreitol (10 μM) in the culture medium. Media changes are accomplished every 3 days or twice per week. The cells can be removed from the protective solution between 1 and 7 days before they are to be used for culture or other purpose.

These techniques have now made it possible to create a variety of Chlamydia-free (CF) organisms; including continuous cell lines called HeLa-CF, HL-CF, H-292-CF, HuEVEC-CF, McCoy-CF, African green monkey and other cell lines that are capable of supporting chlamydial growth. Various CF strains of mice, rabbits and other animal models for research use can be produced.

Because Chlamydia is highly infectious, organisms which have been cleared of extracellular, replicating and cryptic infections must be protected from exposure to viable EBs if the organisms are to remain clear. The inventors have discovered that many of the nutrients and other materials used to maintain continuous cell lines are contaminated with viable Chlamydia EBs. For example, every lot of fetal calf serum has tested positive for the Chlamydia MOMP gene by PCR. Since extensive digestion is required for isolation of the DNA, we have concluded it is bound in EBs. *C. pneumoniae* can also be cultured directly from fetal calf serum. Thus, it is necessary to inactivate EBs in these materials, such as culture media and nutrients, used to maintain the Chlamydia-free status of the organism. Collectively these materials are referred to herein as "maintenance materials". In one embodiment, nutrients and culture media are subjected to gamma irradiation to inactivate Chlamydia therein. Preferably, the material should be irradiated for a period of time sufficient to expose the material to at least 10,000 rads of gamma radiation. It is important for the material to be contained in vessels that do not absorb high energy radiation. The preferred vessel is plastic. In another embodiment, the maintenance materials are treated with a disulfide reducing agent (e.g., dithiothreitol (10 μM) for about 30 minutes) and then the treated maintenance materials are passed through a standard submicron (e.g., about 0.45 microns) filtration system. The reducing agent causes any EBs to expand to the size where a 0.45 micron filter will block their passage. Examples of suitable disulfide reducing agents include, but are not limited to, dithiothreitol, succimer, glutathione, DL-penicillamine, D-penicillamine disulfide, 2,2'-dimercaptoadipic acid, 2,3-dimercapto-1-propone-sulfide acid. In yet another embodiment, maintenance materials are treated with a disulfide reducing agent, preferably dithiothreitol (e.g., about 10 μM concentration), before the materials are passed through a filtration system to remove Chlamydia therefrom.

In order to insure that research tools, such as cell lines and animals, remain Chlamydia-free, an assay has been designed to evaluate whether an organism is Chlamydia-free. The method comprises obtaining a sample of cells or tissue culture; culturing the cells in the absence of cycloheximide and determining the presence or absence of Chlamydia nucleic acid by a suitable amplification technique, such as PCR. The absence of nucleic acid amplification signal is indicative that the status of the organism is Chlamydia-free.

Susceptability Testing for Evaluating Active Agents Against Various Forms of Chlamydia This invention pertains to novel approaches for the susceptibility testing of Chlamydia species that are necessitated by the complex life cycle of the chlamydial pathogen as well as by its diverse, extensive, and heretofore unappreciated ability to cause chronic, cryptic, and persistent systemic infections that are refractory to short duration therapy with conventional single agents. The inventors have discovered that successful eradication of chronic/systemic chlamydial infections can be predicted by using the described unique methods for in vitro and in vivo susceptibility testing.

The invention is based upon the discovery that current susceptibility testing methods for Chlamydiae do not accurately predict the ability of antimicrobial agents to successfully and totally eradicate chronic chlamydial infections. This is because the current susceptibility testing methods measure only replication of chlamydia and ignores the well-known "cryptic phase" (28–33) in which Chlamydiae are not actively replicating. Moreover, it has also been discovered that the so-called "cryptic phase" of Chlamydiae includes multiple and different phases. The following are phases of the chlamydial life cycle in which the Chlamydiae are not replicating: an initial intranuclear phase in which elementary bodies (EBs) transition to reticulate bodies (RBs), an intracytoplasmic phase in which there is a transition of the RB phenotype to the EB phenotype, an intracytoplasmic phase with a nonreplicating, but metabolizing RB, and intracellular/extracellular EB phases in which there is neither replication nor metabolsim. In order to assess the cumulative and long term effect of antimicrobial therapy on these multiple life phases, unique in vitro and in vivo susceptibility test methods have been developed and are described herein.

The term "susceptibility" as used herein is intended to mean a physiological response of an organism to an environmental or chemical stimuli. The desired physiological response to stimuli is one which adversely affects the pathogen's viability to replicate or reside within the host cell and, ideally, would result in the complete elimination (i.e., death) of that pathogen.

A. In Vitro Methodology

One aspect of the invention pertains to methods for evaluating the susceptibility of the distinct phases and stages of the life cycle of Chlamydia, to a particular agent (s), particularly the cryptic phase, since prior techniques have failed, heretofore, to appreciate the need for drugs that can clear infected cells of cryptic Chlamydia. A preferred drug screening method which accomplished this objective utilizes tissue culture cells, in the absence of cycloheximide in order to encourage cryptic infection. Cryptic infection is uncommon in cells used in standard cell culture susceptibility techniques because Chlamydia in cycloheximide-paralyzed cells need not compete with the host cell for metabolites and hence are encouraged to replicate.

The in vitro method uses standard tissue culture cells, but without the addition of cycloheximide. Moreover, the chlamydiae are allowed to replicate for several days prior to the addition of at least one test agents. A "test agent" can be any compound to be evaluated as an antichlamydial agent for its ability to significantly reduce the presence of Chlamydia in living cells. For example, a test agent can include, but is not limited to, antibiotics, antimicrobial agents, antiparasitic agents, antimalarial agent, disulfide reducing agents and antimycobacterial agents. The test agent(s) is/are replaced when needed for the duration of the incubation time (days to weeks) to ensure that the test agent is present and has not been otherwise degraded. Antimicrobial agent(s) (test agent) is then added to the replicating cells. The antimicrobial agents/growth medium are periodically replaced for the duration of the incubation time, which is preferably weeks rather than days. Finally, the end point after the prolonged incubation time is the complete absence of chlamydial DNA, as determined by a nucleic acid amplification technique, such as the polymerase chain reaction (PCR) methodology. Standard nucleic acid amplification techniques (such as PCR) are used to ascertain the presence or absence of signal for chlamydial DNA encoding MOMP or other unique Chlamydia protein to determine whether the test agent or combination of agents is/are effective in reducing Chlamydia infection. The loss of signal (i.e., below the detectable level of the nucleic acid amplification technique) in cells with antibiotic(s) versus its presence in controls is an indication of efficacy of the agent or combination of agents against Chlamydia.

Accordingly, the susceptibility test of this invention can be used to identify an agent or agents which are effective against any particular species of Chlamydia and can be used to identify agent(s) effective against the cryptic form of the pathogen, i.e., is capable of inhibiting or eliminating the cryptic form of the pathogen. Agents that are effective against Chlamydia, as ascertained by the susceptibility testing protocols described herein, can be used as part of a therapy for the management of Chlamydia infections. Suitable therapeutic protocols are described in detail below, with a particular focus on targeting agents toward specific stages of the chlamydial life cycle.

The methods described herein are unique because they evaluate the activity of antimicrobial agents in the absence of cycloheximide which provides a more clinically relevant intracellular milieu. For example, any energy-dependent host cell membrane pumps which might move antimicrobial agents in or out of the cell are inactivated by the use of cycloheximide. The methods described herein are unique because they utilize culture medium which has previously been inactivated. The methods are also unique because they measures the effect of a prolonged duration of exposure to the antimicrobial agent(s) after the intracellular infection by chlamydiae has become established. Finally, the method is unique because it measures the presence/absence of chlamydial DNA as the endpoint, for example by measuring PCR signal. By using complete eradication of chlamydial DNA as an endpoint, the susceptibility test confirms that all phases of Chlamydiae have been eradicated as opposed to merely a temporary halt in replication.

When PCR is the preferred methodology used to evaluate assay endpoint, the PCR method can be enhanced by the unique application of a reducing agent, such as dithiothreitol (DTT), in order to uncoat chlamydial EBs and hence allow exposure of the DNA. In other words, DTT permits the EB coating to rupture. By using an assay for DNA in which EBs are specifically uncoated, the susceptibility test endpoint assesses the presence or absence of EBs as well as the presence or absence of both replicating and nonreplicating RBs. Thus, this approach for chlamydial susceptibility testing allows quantitative antimicrobial susceptibility assays of single and combination agents in which the cumulative effect of the agent(s) on the complete eradication of all life phases is measured. Examples of results obtained with this in vitro method are described below.

In one embodiment, a suitable nucleic acid assay for identifying agents effective against the cryptic form of chlamydia comprises, in the presence of agent(s) to be tested, subjecting cultured cells to protease/reducing agent (e.g., dithiotreitol) and protease digestion or guanidine isothiocyanate (also known as guanidine thiocyanate) for a prescribed period of time; extracting DNA from the treated solution; exposing DNA to appropriate polymerase, dNTPs and primers for DNA amplification of MOMP or other protein of the Chlamydia species; and determining the presence or absence of amplified DNA by visualizing the ethidium bromide treated DNA product by gel electrophoresis, for example. In particular embodiments, the Chlamydia species is *C. pneumoniae* and the appropriate primers are CHLMOMPDB2 and CHLMOMPCB2.

The invention further relates to a method of identifying cells containing the cryptic form of a Chlamydia species by a nucleic acid amplification technique (e.g., PCR) comprising subjecting cultured cells to protease digestion; stopping protease activity; exposing cells to appropriate heat-stable DNA polymerase, dNTPs and labeled primers (e.g., 3'-biotin labeled, 5'-biotin labeled) for amplification of DNA encoding MOMP of the Chlamydia species; washing the cells; exposing the cells to a reporter molecule (e.g., strepavidin-conjugated signal enzyme); exposing the cells to an appropriate substrate for the reporter molecule (e.g., conjugated enzyme); and visualizing the amplified DNA encoding MOMP by visualizing the product of the reaction.

The invention pertains to a method of identifying cells containing the cryptic form of Chlamydia. The method comprises treating cultured cells, thought to be infected with Chlamydia, with a disulfide reducing agent; subjecting cultured cells to protease digestion; exposing cells to appropriate polymerase, dNTPs and primers for DNA amplification of nucleic acid encoding of a chlamydial protein; exposing the cells to a reporter molecule enzyme; exposing the cells to an appropriate substrate for the reporter enzyme; and determining the presence of the cryptic form of Chlamydia by visualizing the amplified DNA encoding a chlamydial protein. Preferably the amplification technique is PCR and the primers are CHLMOMPDB2 and CHLMOMPCB2 of *Chlamydia pneumoniae*.

A similar method can be used as an assay for identifying an agent which is effective against the cryptic form of Chlamydia. Accordingly, the method comprises treating cultured cells grown in the absence of cycloheximide, thought to be infected with Chlamydia, with a disulfide reducing agent; allowing the Chlamydia to replicate; adding a test agent; subjecting cultured cells to protease digestion; exposing cells to appropriate polymerase, dNTPs and primers for DNA amplification of a gene encoding chlamydial protein; exposing the cells to a reporter molecule enzyme; exposing the cells to an appropriate substrate for the reporter enzyme; and determining the presence of cryptic form of Chlamydia by visualizing the amplified DNA encoding a chlamydial protein, such as MOMP.

A detailed description of primers, PCR techniques and other methodologies useful for the present invention are provided in U.S. patent application Ser. No. 09/025,596 entitled "Identification of Antigenic Peptide Sequences" filed concurrently herewith; the entire teachings of this application are incorporated herein by reference.

B. In Vivo Methodology

In another aspect of the invention, the susceptibility test can be used to evaluate the status of a human or animal undergoing therapy for the management of Chlamydia infection. For example, a biological material is isolated from the human or animal undergoing combination therapy. The biological material is treated such that the Chlamydia is isolated therefrom. This chlamydial isolate is allowed to infect Chlamydia free cells. These infected cells are. then exposed to the combination of agents being used in the individual undergoing combination therapy. Alternatively, the individual's serum containing the antimicrobial agents can be added to the infected cells as a "serum bactericidal test" for intracellular chlamydial infection.

The in vivo method uses the murine model although other animals such as rats or rabbits can be used. In this method, mice (or any other animal) are inoculated intranasally with $2 \times 10^5$ chlamydial EBs per ml. The inventors have confirmed the work of Yang and colleagues (15) in which intranasal inoculation of chlamydial EBs results in systemic dissemination and, in particular, causes infection of the spleen. The inventors have discovered that this systemic dissemination also results in the presence of EBs in the blood of the mice. Therefore, infectivity can be measured by blood culture or by serum/whole blood PCR for chlamydial DNA. Systemic infection is also confirmed and monitored by the presence of elevated IgM and IgG antibody titers. After the systemic murine infection has been established, antimicrobial agents are given to the mice. This is most easily done by adding the antibiotics to the drinking water. The effect of antichlamydial therapy is monitored by serum/whole blood PCR. When the serum/PCR assay suggests eradication of chlamydiae from the bloodstream, the mice are sacrificed and PCR for chlamydial DNA is done on lung, heart, liver, and spleen homogenates. This method is unique because it measures the complete eradication of all life forms of chlamydiae in known murine target organs for chlamydial infection. This in vivo susceptibility method has revealed, for example, that antimicrobial therapy with the triple agents, INH, metronidazole and penicillamine, can completely eradicate *C. pneumoniae* from infected mice in four months. Moreover, following complete eradication of chlamydiae, multiple attempts to reinfect these cured mice via intranasal inoculation have proven unsuccessful. This suggests that effective therapy and complete eradication results in the development of protective immunity, and that effective therapy is therefore a way to create effective immunity.

Performing PCR for chlamydial DNA on homogenates of other organ systems can be used to determine the effectiveness of particular antibiotic combinations in eradicating chlamydial infection in those organ systems. Establishment of prior chlamydial infection of those systems can be done by either biopsy or antibody-enhanced radiological imaging. Alternatively, prior infection can be determined statistically by performing PCR for chlamydial DNA on homogenates of the same organ systems in a similarly inoculated but untreated control population. Organ-specific susceptibility is determined by comparing rates of positive PCR assays in the control and treated populations.

An alternative or complementary method of determining the presence of cryptic chlamydial infections in an animal or cell culture is to expose the culture to chlamydia-stimulating compounds. Such compounds include (but are not limited to) cycloheximide, corticosteriods (such as prednisone) and other compounds which are known to stimulate reactivation of cryptic intracellular infections, and disulfide reducing agents (such as dithiotreitol) and other chemicals which cause EBs to turn into RBs. Once the cryptic forms have entered a more active phase, they can be detected using standard detection techniques such as visual detection of inclusion bodies, immunochemical detection of chlamydial antigen, or reverse transcriptase-PCR.

Antichlamydial Therapy Directed Toward the Initial Stage of Chlamydia Infection

A number of effective agents that are specifically directed toward the initial phase of chlamydial infection (i.e., transition of the chlamydial EB to an RB) have been identified. This growth phase, unlike that of the replicating chlamydial microorganism, which uses host cell energy, involves electrons and electron transfer proteins, as well as nitroreductases. Based upon this, it has been shown that the initial phase of Chlamydia infection is susceptible to the antimicrobial effects of nitroimidazoles, nitrofurans and other agents directed against anaerobic metabolism in bacteria.

Nitroimidazoles and nitrofurans are synthetic antimicrobial agents that are grouped together because both are nitro ($NO_2$—) containing ringed structures and have similar antimicrobial effects. These effects require degradation of the agent within the microbial cell such that electrophilic radicals are formed. These reactive electophilic intermediates then damage nucleophilic protein sites including ribosomes, DNA and RNA. Nitroimidazoles and nitrofurans currently are not considered to possess antimicrobial activity against members of the Chlamydia species. This lack of antimicrobial activity, however, is due to the fact that conventional susceptibility testing methods only test for effect on the replicating form of Chlamydia species.

Examples of suitable nitroimidazoles include, but are not limited to, metronidazole, tinidazole, bamnidazole, benznidazole, flunidazole, ipronidazole, misonidazole, moxnidazole, ronidazole, sulnidazole, and their metabolites, analogs and derivatives thereof. Metronidazole is most preferred. Examples of nitrofurans that can be used include, but are not limited to, nitrofurantoin, nitrofurazone, nifurtimox, nifuratel, nifuradene, nifurdazil, nifurpirinol, nifuratrone, furazolidone, and their metabolites, analogs and derivatives thereof. Nitrofurantoin is preferred within the class of nitrofurans.

Throughout this application and for purposes of this invention, "metabolites" are intended to embrace products of cellular metabolism of a drug in the host (e.g., human or animal) including, but not limited to, the activated forms of prodrugs. The terms "analogs" and "derivatives" are intended to embrace isomers, optically active compounds and any chemical or physical modification of an agent, such that the modification results in an agent having similar or increased, but not significantly decreased, effectiveness against Chlamydia, compared to the effectiveness of the parent agent from which the analog or derivative is obtained. This comparison can be ascertained using the susceptability tests described herein.

Cells to be treated can already be cryptically infected or they can be subjected to stringent metabolic conditions which cause or induce the replicating phase to enter the cryptic phase. Such stringent conditions can include changing environmental/culturing conditions in the instance where the infected cells are exposed to γ-interferon; or by exposing cells to conventional antimicrobial agents (such as macrolides and tetracyclines) which induce this cryptic phase of chlamydial infection in human host cells.

Novel Antichlamydial Therapy Directed Toward the Replicating Phase of Chlamydia Infection A unique class of antichlamydial agents that is effective against the replicating phase of Chlamydia (and possibly against some stages of the cryptic stage) have been identified using the susceptability tests described herein. This novel class of agents comprises ethambutol and isonicotinic acid congeners which include isoniazid (INH), isonicotinic acid (also known as niacin), nicotinic acid, pyrazinamide, ethionamide, and aconiazide; where INH is most preferred. Although these are currently considered effective only for mycobacterial infections, due in part to currently available susceptability testing methodologies, it has been discovered that these agents, in combination with other antibiotics, are particularly effective against Chlamydia. It is believed that the isonicotinic acid congeners target the constitutive production of catalase and peroxidase, which is a characteristic of microorganisms, such as mycobacteria, that infect monocytes and macrophages. Chlamydia can also successfully infect monocytes and macrophages.

Using INH to eradicate Chlamydia from macrophages and monocytes subsequently assists these cells in their role of fighting infection. However, these agents appear to be less effective, in vitro, against the cryptic phase. Thus, ethambutol, INH and other isonicotinic acid congeners ideally should be used in combination with agents that target other phases of the chlamydial life cycle. These isonicotinic acid congeners are nevertheless excellent agents for the long term therapy of chronic/systemic chlamydial infection generally, and in particular to chlamydial infection of endothelial and smooth muscle cells in human blood vessels.

INH and its congeners can be used to clear infection from monocytes and/or macrophages. When monocytes and macrophages are infected by Chlamydia, they become debilitated and cannot properly or effectively fight infection. It is believed that, if the chlamydial infection, per se, is cleared from these cells, then the monocytes and macrophages can resume their critical roles fighting chlamydial or other infection(s). Thus, patient responsiveness to combination therapy can be optimized by the inclusion of isonicotinic acid congeners. Accordingly, one aspect of the invention provides a specific method for reempowering monocytes or macrophages that have been comprised by a Chlamydia infection and, in turn, comprise treating the infection in other sites. Such compromised macrophages or monocytes can be activated by treating the chlamydia infection by contacting the infected macrophages and/or monocytes with an antichlamydial agent.

Therapy Directed Toward Elementary Bodies of Chlamydia

As discussed above, it has been discovered that adverse conditions, such as limited nutrients, antimicrobial agents, and the host immune response, produce a stringent response in Chlamydia. Such adverse conditions are known to induce stringent responses in other microorganisms (C. W. Stratton, In: *Antibiotics in Laboratory Medicine*, Fourth Edition. Lorian V (ed) Williams & Wilkins, Baltimore, pp 579–603 (1996)) and not surprisingly induce a stringent response in Chlamydia. This stringent response in Chlamydia alters the morphological state of the intracellular microorganism and creates a dormant form, the intracellular EB, which then can cryptically persist until its developmental cycle is reactivated. Conversely, the host cell may lyse and allow the EBs to reach the extracellular milieu. Thus, it is necessary to utilize a combination of agents directed toward the various life stages of Chlamydia and, in particular, against the elementary body for successful management of infection.

During the unique chlamydial life cycle, it is known that metabolically-inactive spore-like EBs are released into the extracellular milieu. Although these released EBs are infectious, they may not immediately infect nearby susceptible host cells until appropriate conditions for EB infectivity are present. The result of this delay in infection is the extracellular accumulation of metabolically-inactive, yet infectious, EBB. This produces a second type of chlamydial persistance referred to herein as EB "tissue/blood load". This term is similar in concept to HIV load and is defined herein as the number of infectious EBs that reside in the extracellular milieu. Direct microscopic visualization techniques, tissue cell cultures, and polymerase chain reaction test methods have demonstrated that infectious EBB are frequently found in the blood of apparently healthy humans and animals. This phenomenon is clearly of great clinical importance in chlamydial infections as these metabolically-inactive EBs escape the action of current antichlamydial therapy which is directed only against the replicating intracellular forms of Chlamydia. The presence of infectious extracellular EBs after the completion of short term, antireplicating phase therapy for chlamydial infections has been shown to result in infection relapse. Thus, the duration and nature of antichlamydial therapy required for management of chlamydial infections is, in part, dictated by the extracellular load of EBs. For purposes of this invention, short term therapy can be approximately two to three weeks; long term therapy in contrast is for multiple months.

As described in previous sections, it is also believed that persistance of chlamydial infections, in part, may be due to the presence of the cryptic form of Chlamydia within the cells. This cryptic intracellular chlamydial form apparently can be activated by certain host factors such as cortisone (Yang et al., Infection and Immunity, 39:655–658 (1983); and Malinverni et al., *The Journal of Infectious Diseases*, 172:593–594 (1995)). Antichlamydial therapy for chronic Chlamydia infections must be continued until any intracellular EBs or other intracellular cryptic forms have been activated and extracellular EBs have infected host cells. This reactivation/reinfection by chlamydial EBs clearly is undesirable as it prolongs the therapy of chlamydial infections, as well as increases the opportunity for antimicrobial resistance to occur.

Physiochemical agents have been identified that can inactivate chlamydial EBs in their respective hosts by reducing disulfide bonds which maintain the integrity of the outer membrane proteins of the EBs. For Chlamydia, disruption of the outer membrane proteins of EBs thereby initiates the transition of the EB form to the RB form. When this occurs in the acellular milieu where there is no available energy source, the nascent RB perishes or falls victim to the immune system. Thus, disulfide reducing agents that can interfere with this process are suitable as compounds for eliminating EBs.

One such class of disulfide reducing agents are thiol-disulfide exchange agents. Examples of these include, but are not limited to, 2,3-dimercaptosuccinic acid (DMSA; also referred to herein as "succimer"); D,L,-β,β-dimethylcysteine (also known as penicillamine); β-lactam (e.g., penicillins, penicillin G, ampicillin and amoxicillin, which produce penicillamine as a degradation product), cycloserine, dithiotreitol, mercaptoethylamine (e.g., mesna, cysteiamine, dimercaptol), N-acetylcysteine, tiopronin, and glutathione. A particularly effective extracellular antichlamydial agent within this class is DMSA which is a chelating agent having four ionizable hydrogens and two highly charged carboxyl groups which prevent its relative passage through human cell membranes. DMSA thus remains in the extracellular fluid where it can readily encounter extracellular EBs. The two thiol (sulfhydryl) groups on the succimer molecule (DMSA) are able to reduce disulfide bonds in the MOMP of EBs located in the extracellular milieu.

Penicillamine can also be used as a disulfide reducing agent to eliminate chlamydial EBs. However, the use of penicillamine may cause undesirable side effects. Thus, as an alternative, those β-lactam agents which are metabolized or otherwise converted to penicillamine-like agents in vivo (i.e., these agents possess a reducing group) can be orally administered to the human or animal as a means of providing a controlled release of penicillamine derivatives, by acid hydrolysis of the penicillin, under physiologic conditions. The in vivo production of penicillamine from the degradation of penicillins undoubtedly accounts for the known in vitro ability of penicillins to reduce or prevent the development of infectious chlamydial EBs in cell cultures.

Currently Recognized Agents Active Against Chlamydia Replication

As chlamydial RBs transform into EBs, they begin to utilize active transcription of chlamydial DNA and translation of the resulting mRNA. As such, these forms of Chlamydia are susceptible to currently used antimicrobial agents. The antichlamydial effectiveness of these agents can be significantly improved by using them in combination with other agents directed at different stages of Chlamydia life cycle, as discussed herein.

Classes of suitable antimicrobial agents include, but are not limited to, rifamycins (also known as ansamacrolides), quinolones, fluoroquinolones, chloramphenicol, sulfonamides/sulfides, azalides, cycloserine, macrolides and tetracyclines. Examples of these agents which are members of these classes, as well as those which are preferred, are illustrated below in Table 5.

TABLE 5

Agents Effective Against the Replicating Phase of Chlamydia

| Drug Class | Examples | Preferred |
|---|---|---|
| Quinolones/<br>Fluoroquinolones | Ofloxacin<br>Levofloxacin<br>Trovafloxacin<br>Sparfloxacin<br>Norfloxacin<br>Lomefloxacin<br>Cinoxacin<br>Enoxacin<br>Nalidixic Acid<br>Fleroxacin<br>Ciprofloxacin | Levofloxacin |
| Sulfonamides | Sulfamethoxazole | Sulfamethoxazole/<br>Trimethoprim |
| Azalides | Azithromycin | Azithromycin |
| Macrolides | Erythromycin<br>Clarithromycin | Clarithromycin |
| Lincosamides | Lincomycin<br>Clindamycin | |
| Tetracyclines | Tetracycline<br>Doxycycline<br>Minocycline<br>Methacycline<br>Oxytetracyline | Minocycline |
| Rifamycins<br>(Ansamacrolides) | Rifampin<br>Rifabutin | Rifampin |

All members of the Chlamydia species, including *C. pneumoniae*, are considered to be inhibited, and some killed, by the use of a single agent selected from currently used antimicrobial agents such as those described above. However, using the new susceptability test, the inventors have found complete eradication of Chlamydia cannot be achieved by the use of any one of these agents alone because none are efficacious against all phases of the Chlamydia life cycle and appear to induce a stringent response in Chlamydia causing the replicating phase to transform into cryptic forms. This results in a persistent infection in vivo or in vitro that can be demonstrated by PCR techniques which assess the presence or absence of chlamydial DNA. Nevertheless, one or more of these currently used agents, or a new agent directed against the replicating phase of Chlamydia, should be included as one of the chlamydial agents in a combination therapy in order to slow or halt the transition of the EB to the RB as well as to inhibit chlamydial replication.

Diseases Associated with Chlamydial Infection

An association has been discovered between chronic Chlamydia infection of body fluids and/or tissues with several disease syndromes of previously unknown etiology in humans which respond to unique antichlamydial regimens described herein. To date, these diseases include Multiple Sclerosis (MS), Rheumatoid Arthritis (RA), Inflammatory Bowel Disease (IBD), Interstitial Cystitis (IC) Fibromyalgia (FM), Autonomic nervous dysfunction (AND, neural-mediated hypotension); Pyoderma Gangrenosum (PG), Chronic Fatigue (CF) and Chronic Fatigue Syndrome (CFS). Other diseases are under investigation correlation between Chlamydia infection and these diseases has only recently been established as a result of the diagnostic methodologies and combination therapies described herein.

Based on this evidence, published evidence of an association between atherosclerosis and Chlamydia (Grupta et al., *Circulation* 96:404–407 (1997)), and an understanding of the impact Chlamydia infections have on infected cells and the immune systems, the inventors have discovered a connection between Chlamydia and a broad set of inflammatory, autoimmune, and immune deficiency diseases. Thus, the invention describes methods for diagnosing and/or treating disease associated with Chlamydia infection, such as autoimmune diseases, inflammatory diseases and diseases that occur in immunocompromised individuals by diagnosing and/or treating the Chlamydia infection in an individual in need thereof, using any of the assays or therapies described herein. Progress of the treatment can be evaluated serologically, to determine the presence or absence of Chlamydia using for example the diagnostic methods provided herein, and this value can be compared to serological values taken earlier in the therapy. Physical improvement in the conditions and symptoms typically associated with the disease to be treated should also be evaluated. Based upon these evaluating factors, the physician can maintain or modify the antichlamydial therapy accordingly. For example, the physician may change an agent due to adverse side-effects caused by the agent, ineffectiveness of the agent, or for other reason. When antibody titers rise during treatment then alternate compounds should be substituted in order to achieve the lower antibody titers that demonstrate specific susceptability of the Chlamydia to the new regimen. A replacement or substitution of one agent with another agent that is effective against the same life stage of Chlamydia is desirable.

The therapies described herein can thus be used for the treatment of acute and chronic immune and autoimmune diseases when demonstrated to have a Chlamydia load by the diagnostic procedures described herein which include, but are not limited to, chronic hepatitis, systemic lupus erythematosus, arthritis, thyroidosis, scleroderma, diabetes mellitus, Graves' disease, Beschet's disease and graft versus host disease (graft rejection). The therapies of this invention can also be used to treat any disorders in which a chlamydial species is a factor or co-factor.

Thus, the present invention can be used to treat a range of disorders in addition to the above immune and autoimmune diseases when demonstrated to be associated with Chlamydial infection by the diagnostic procedures described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis.

Among the various inflammatory diseases, there are certain features of the inflammatory process that are generally agreed to be characteristic. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis, chronic vascular headaches (including migraines, cluster headaches and tension headaches) and pneumonia when demonstrated to be pathogenically related to Chlamydia infection.

Treatable disorders when associated with Chlamydia infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo palsy; Cerebellar and Spinocerebellar Disorders, such as astructural lesions of the cerebellum; spinocerebellar degenerations (spinal ataxia, Friedreich's ataxia, cerebellar cortical degenerations, multiple systems degenerations.(Mencel, Dejerine-Thomas, Shi-Drager, and Machado Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dermentia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides)); carcinomas (such as colon carcinoma) and metastases thereof; cancer-related angiogenesis; infantile hemangiomas; alcohol-induced hepatitis. Ocular neovascularization, psoriasis, duodenal ulcers, angiogenesis of the female reproductive tract, can also be treated when demonstrated by the diagnostic procedures described herein to be associated with Chlamydial infection.

An immunocompromised individual is generally defined as a person who exhibits an attenuated or reduced ability to mount a normal cellular or humoral defense to challenge by infectious agents, e.g., viruses, bacterial, fungi and protozoa. Persons considered immunocompromised include malnourished patients, patients undergoing surgery and bone narrow transplants, patients underoing chemotherapy or radiotherapy, neutropenic patients, HIV-infected patients, trauma patients, burn patients, patients with chronic or resistant infections such as those resulting from myeloodysplastic syndrome, and the elderly, all of who may have weakened immune systems. A protein malnourished individual is generally defined as a person who has a serum albumin level of less than about 3.2 grams per deciliter (g/dl) and/or unintentional weight loss greater than 10% of usual body weight.

The course of therapy, serological results and clinical improvements from compassionate antichlamydial therapy in patients diagnosed with the diseases indicated were observed and are reported in Example 5. The data provides evidence to establish that treatment of Chlamydia infection results in the serological and physical improvement of a disease state in the patient undergoing combination therapy. These observations were consistent among a variety of different diseases which fall within a generalized disease class.

Other Diseases of Unknown Etiology with New Evidence for a Chlamydia Pneumoniae Etiology Both *C. trachomatis* and *C. psittaci* exhibit a protean disease complex dependent on different serovars. One known basis for this diversity to date is the amino acid sequence of the MOMP. FIG. 1 shows a sequence alignment of various Chlamydia MOMPs. Note that the size and sequence are relatively homologous except for the four variable regions that are responsible for the serovar (serotype) basis of classification. Further, it has been discovered that *C. pneumoniae* infects blood vessel endothelial cells from which EBs are released in the blood stream. In addition, macrophages are known targets for *C. pneumoniae* and may serve as reservoirs and provide an additional mechanism of transmission. *C. pneumoniae* is thus able to spread throughout the human body, establishing infection in multiple sites and in multiple organ systems. Infected sites may exist for an extended period without inducing symptoms that are noticed by the patient or by an examining physician. Sequence variability of MOMPs or other chlamydial antigens may provide a basis for organ specificity while other chlamydial proteins, such as the 60K and 70K heat shock proteins or LPS, may influence immune response.

*C. psittaci* and *C. pecorum* are known to cause a host of infections in economically significant animals. Thus, the teachings of this invention are relevant to animals. Throughout this application and for purposes of this invention, "patient" is intended to embrace both humans and animals. Virtually all rabbits and mice tested to date have PCR signals for *C. pneumoniae*. They can be used as appropriate animal models for treatment using specific combination antibiotics to improve therapy. (Banks et al., *Ameri. J. of Obstetrics and Gynecology* 138(7Pt2):952–956 (1980)); (Moazed et al., *Am. J. Pathol.* 148(2):667–676 (1996)); (Masson et al., *Antimicrob. Agents Chemother.* 39(9):1959–1964 (1995)); (Patton et al., *Antimicrob. Agents Chemother.* 37(1):8–13 (1993)); (Stephens et al., *Infect. Immun.* 35(2):680–684 (1982)); and (Fong et al., *J. Clin. Microbiol* 35(1):48–52 (1997)).

Coupled with these developments are the recently developed rabbit models of coronary artery disease, where rabbits exposed to *C. pneumoniae* subsequently develop arterial plaques similar to humans (Fong et al., *J. Clin. Microbiol.* 35:48–52 (1997)). Most recently, a study at St. George's Hospital in London found that roughly ¾ of 213 heart attach victims have significant levels of antibodies to *C. pneumoniae* antibody and that those that have such antibodies achieve significantly lower rates of further adverse cardiac events when treated with antibiotics (Gupta et al., *Circulation* 95:404–407 (1997)). Taken together, these three pieces of evidence (the bacteria found in diseased tissue, inoculation with the bacteria causes diseases, and treating for the bacteria mitigates disease) make a case for a causal connection.

Adjunct Agents used in Conjunction with the Combination Therapy

In addition to the combination therapies discussed above, other compounds can be co-administered to an individual undergoing antichlamydial therapy for the management of chronic/systemic infection. For example, it may be desirable to include one or a combination of anti-inflammatory agents and/or immunosuppressive agents to ameliorate side-effects that may arise in response to a particular antichlamydial agent, e.g., Herxheimer reactions. Initial loading with an anti-inflammatory steroid can be introduced to minimize side-effects of the antichlamydial therapy in those patients in which clinical judgment suggests the possibility of serious inflammatory sequelae.

Suitable anti-inflammatory agents (steroidal and nonsteroidal agents) include, but are not limited to, Prednisone, Cortisone, Hydrocortisone and Naproxin. Preferably the anti-inflammatory agent is a steroidal agent, such as Prednisone. The amount and frequency of administration of these adjunct compounds will depend upon patient health, age, clinical status and other factors readily apparent to the medical professional.

Vitamin C (2 gms bid) has also been introduced based on the report that Vitamin C (ascorbic acid) at moderate intracellular concentrations stimulates replication of *C. trachomatis* (Wang et al., *J. Clin. Micro.* 30:2551–2554 (1992)) as well as its potential effect on biofilm charge and infectivity of the bacterium and specifically the EB (Hancock, R. E. W., *Annual Review in Microbiology*, 38:237–264 (1984)).

Modes of Administration

Based upon the ability of the combination therapy of this invention to improve both the serological and physical status of a patient undergoing treatment, pharmaceutical compositions or preparations can be made comprising at least two different agents chosen from the following groups: a) at least one agent effective against elementary body phase of chlamydial life cycle (e.g., disulfide reducing agents); b) at least one agent effective against replicating phase of chlamydial life cycle (e.g., antimycobacterial agents); and c) at least one agent effective against cryptic phase of chlamydial life cycle (e.g., anerobic bactericidal agents). As discussed in greater detail below, the agents can be formulated in a physiologically acceptable vehicle in a form which will be dependent upon the method in which it is administered.

In another aspect, the invention pertains to a combination of agents comprising at least two agents, each of which is effective against a different phase of the chlamydial life cycle, as previously discussed. The combination of antichlamydial can be used in the management of chlamydial infection or prophylaxis thereof to prevent recurrent infection. The combination of agents can be in the form of an admixture, as a pack (discussed in detail below) or individually, and/or by virtue of the instruction to produce such a combination. It should be understood that combination therapy can comprise multiple agents that are effective within a particular phase of the chlamydial life cycle. The combination of antichlamydial agents can further comprise immunosuppressants, anti-inflammatory agents, vitamin C and combinations thereof.

In a preferred embodiment, if only one antichlamydial agent is elected to be used in an asymptomatic patient to reduce/prevent chronic infection, this agent is a reducing agent, such as penicillamine.

The novel therapeutic methods described herein can be used to ameliorate conditions/symptoms associated with the disease states described above, when the disease is onset or aggravated by infection by Chlamydia. The agents of this invention can be administered to animals including, but not limited to, fish, amphibians, reptiles, avians and mammals including humans. Compounds and agents described herein can be administered to an individual using standard methods and modes which are typically routine for the disease state.

Combination(s) of antichlamydial agents of this invention can be used for the manufacture of a medicament for simultaneous, separate or sequential use in managing chlamydial infection or prophylaxis thereof. The agents can also be used for the manufacture of a medicament for therapy of a disease associated with chlamydia infection, such as autoimmune disease, inflammatory disease, immunodeficiency disease.

The agents can be administered subcutaneously, intravenously, parenterally, intraperitoneally, intradermally, intramuscularly, topically, enteral (e.g., orally), rectally, nasally, buccally, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal, intestinal mucosa, bronchial mucosa) administration, via nose drops, aerosols, inhalants, nebulizers, eye drops or suppositories can be used. The compounds and agents of this invention can be administered together with other biologically active agents.

In a specific embodiment, it may be desirable to administer the agents of the invention locally to a localized area in need of treatment; this may be achieved by, for example, and not by way of limitation, local infusion during surgery, topical application (e.g., for skin conditions such as psoriasis), transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints.

In a specific embodiment when it is desirable to direct the drug to the central nervous system, techniques which can opportunistically open the blood brain barrier for a time adequate to deliver the drug there through can be used. For example, a composition of 5% mannitose and water can be used. In another embodiment, the agents can be delivered to a fetus through the placenta since many of the agents are small enough to pass through the placental barrier.

The present invention also provides pharmaceutical compositions. Such compositions comprise a therapeutically (or prophylactically) effective amount of the agent, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The drug may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of agents which will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

Diagnostic Reagents

The invention also provides a diagnostic reagent pack or kit comprising one or more containers filled with one or more of the ingredients used in the assays of the invention. Optionally associated with such container(s) can be a notice in the form prescribed by a governmental agency regulating the manufacture, use or sale of diagnostic products, which notice reflects approval by the aggency of manufacture, use of sale for human administration. The pack or kit can be labeled with information regarding mode of administration, sequence of execution (e.g., separately, sequentially or concurrently), or the like. The pack or kit can be a single unit assay or it can be a plurality of unit assays. In particular, the agents can be separated, mixed together in any combination, present in a single fial or tablet. For the purpose of this invention, unit assays is intended to mean materials sufficient to perform only a single assay.

The invention will be further illustrated by the following non-limiting examples of diagnostic and therapeutic methods. All percentages are by weight unless otherwise specified.

EXAMPLES

Example 1

Polymerase Chain Reaction (PCR) for the Full Length MOMP Gene of C. pneumoniae and Other Species of Chlamydia (Diagnostic)

a. Solution PCR

Serum, blood or tissue samples were pre-incubated in the presence of 10 $\mu$M dithiothreitol at room temperature for 2 hours to reduce the disulfide bonds and facilitate release of the outer shell of the elementary bodies. CSF and other body fluids are also suitable for use as. described. Other suitable reducing agents for use in this step include, but are not limited to, succimer and glutathione (e.g., including, but not limited to, glutathione esters, other analogs and deriviatives). The failure to include a reducing agent initially may result in a negative PCR signal following the protease digestion step. Appropriate concentrations of these reducing agents can be readily determined by the skilled artisan without undue experimentation using the 10 μM concentration of dithiothreitol as a guideline. Alternatively, guanidine isothiocyanate may be substituted for the disulfide reduction/protease step. Table 6 shows the effect of various reducing agents on susceptibility of EBs to proteinase K digestion in order to allow DNA extraction for PCR amplification.

TABLE 6

Effect of various reducing agents on susceptibility of EBs to proteinase K digestion in order to allow DNA extraction for PCR amplification.

| Reducing Agent | Concentration | PCR Signal[a] |
|---|---|---|
| Dithiothreitol | 10 mM | + |
| | 1 mM | + |
| | 100 μM | + |
| | 10 μM | + |
| | 1 μM | + |
| Succimer | 10 mM | − |
| | 1 mM | + |
| | 100 μM | + |
| | 10 μM | + |
| | 1 μM | − |
| DL-Penicillamine | 10 mM | − |
| | 1 mM | − |
| | 100 μM | + |
| | 10 μM | − |
| | 1 μM | − |
| D-Penicillamine disulfide | 10 mM | + |
| | 1 mM | − |
| | 100 μM | − |
| | 10 μM | − |
| | 1 μM | − |
| 2,3-Dimercapto-1-Propone-sulfide acid | 10 mM | − |
| | 1 mM | − |
| | 100 μM | + |

TABLE 6-continued Effect of various reducing agents on susceptibility of EBs to proteinase K digestion in order to allow DNA extraction for PCR amplification.

| Reducing Agent | Concentration | PCR Signal[a] |
|---|---|---|
|  | 10 µM | − |
|  | 1 µM | − |
| Meso-2,2'-Dimercapto adipic acid | 10 mM | + |
|  | 1 mM | + |
|  | 100 µM | + |
|  | 10 µM | + |
|  | 1 µM | − |
| Glutathione | 10 mM | − |
|  | 1 mM | wk+ |
|  | 100 µM | − |
|  | 10 µM | +/− |
|  | 1 µM | +/− |
| Control | 0 | − |

[a]All assays performed on control serum #1154, which on repeated assay without reducing agents, yields a negative PCR signal for the 1.2 kB MOMP gene of C. pneumoniae. Analysis on agarose gel with ethidium bromide visualization under UV light.

Serum, blood, or tissue samples are lysed overnight at 37° C. in the presence of SDS which inhibits DNAses and proteinase K which digests protein (i.e., 2×cell lysis buffer: 1% SDS, 0.2 M NaCl, 10 mM EDTA, 20 mM Tris-KCl, pH 7.5 plus proteinase K to a final concentration of 20 mg/ml). Following digestion, the lysate is extracted ×1 with phenol followed by chloroform extraction ×2. DNA is precipitated from the final aqueous phase by the addition of 1/10 volume Na acetate (3 M) and 2–2.5 volume of cold ethanol. The DNA is pelleted by centrifugation and the DNA is resuspended in 10–20 ml water with PCR amplification performed in the same microtube. The entire gene of MOMP (1.2 kb) is amplified using the CHLMOMPDB2 coding strand primer (5'-ATGAAAAAAC TCTTAAAGTC GGCGTTATTA TCCGCCGC; SEQ ID NO. 41) and the CHLMOMPCB2 complimentary strand primer (5'-TTAGAATCTG AACTGACCAG ATACGTGAGC AGCTCTCTCG; SEQ ID NO. 42). Alternatively, shortened primers can be used by making suitable modifications in the primer:DNA hybridization temperature for PCR detection only. The appropriate primer selection, however, may result in the absence of signal if an unknown strain with mutations in one or both primer binding regions is present. The frequency of positive signals using the preferred primers which amplify the full length MOMP gene suggests that mutations in these regions of C. pneumoniae is rare. Standard conditions for this gene product in a 50-µl volume is 35 cycles with 1 second ramp times between steps of 94° C. for 1 minute, 58° C. for 2 minutes and 74° C. for 3 minutes. The PCR reaction used 0.1 mM of each primer in Vent buffer with 200 mM of each dNTP, and 1.0 U Vent DNA polymerase. Amplified DNA is separated and identified by electrophoresis in 1.2% agarose or 6% polyacrylamide gels run in the TBE buffer (88 mM Tris-borate, 89 mM boric acid, 2 mM EDTA) at 120 volts for 1 hour. DNA bands are identified by ethidium bromide staining and UV light detection. Product specificity has been verified by restriction enzyme analysis of cleavage products as well as DNA sequence analysis. Negative controls consist of amplification of lysis buffer extracts. Extreme care must be exercised to screen all components of the cell lysis and amplification buffer components to exclude contaminant MOMP DNA which are common contaminants in such lab and molecular biology grade chemicals.

b. In Situ PCR

This procedure identifies individual cells containing RB and cryptic forms of C. pneumoniae. Cultured cells are adhered to glass slides with formalin, or formalin fixed tissue sections embedded in paraffin are adhered to glass slides and subjected to protease digestion (i.e., pepsin, trypsin, chymotrypsin, or other specific proteases). Each digestion time and pH (i.e., pepsin at pH 2.5 or trypsin at pH 7–8, etc.) with a standard concentration of each protease must be evaluated for each tissue type for optimal digestion times. Protease activity is stopped by washing and/or pH change and the target cells exposed to Taq polymerase, dNTPs, and primers. For the MOMP gene the primers CHLMOMPDB2 and CHLMOMPCB2 have been engineered with a biotin at the 5'-terminus. For in situ PCR, using biotin labels incorporated at the 5'-terminus of the amplification primers, each DNA chain amplification results in each double strand DNA containing 2 molecules of biotin. Standard conditions of amplification are identical to solution PCR described above. Following the end of the PCR cycle, the slides are washed and exposed to strepavidin-β-galactosidase (or other strepavidin conjugated signal enzyme). Visualization of the amplified MOMP gene is accomplished by bound enzyme hydrolysis of soluble substrate yielding an insoluble product which can then be visualized by standard light microscopy.

Alternatively, other specific DNA sequences, including subsections of the full MOMP gene (e.g., subsections including gene sequences for the peptides in FIG. 4) can be used, although the above-described sequence is the preferred embodiment since the large product produced (1.2 kb) prevents diffusion that may be encountered with smaller DNA amplifications. Similarly, other detection labels can be incorporated (i.e., fluorescein, for example) at the 5'-end or dixoxigenin & UTP can be incorporated within the amplified DNA. Alternatively to labeling the product, specific hybridization probes to constant regions of the amplified DNA can be used to identify an amplified product. This latter method has particular utility for the construction of automated laboratory equipment for solution-based PCR. For example, strepavidin-coated ELISA plates can be used to capture one or both strands of a biotin 5'-labeled DNA with detection by fluorescence of a fluorescen or other incorporated fluorophore detection probe.

Example 2

Enzyme Linked Immuno Sorbent Assay (ELISA; Diagnostic)

a. Recombinant MOMP-based ELISA

The full length MOMP gene of C. pneumoniae was directionally cloned into the pET expression plasmid at the NCOI and NOTI restriction sites using primers to introduce these unique restriction sites into the MOMP ends. Primer sequences are as follows:

CPOMPDNCO (Coding strand): 5'-AGCTTACCAT GGCTAAAAAA CTCTTAAAGT CGGCGTTATT ATCCG-3' (SEQ ID NO. 43)

CPOMP_CNOT (complimentary strand): 5'-ATATGCGGCC GCTCATAGAA TCTGAACTGA CCAGATACG-3' (SEQ ID NO. 43)

The construction of the MOMP insert into the pET expression vector (Novagen. Inc.) yields, on transformation of permissive E. coli, an amino terminal thioredoxin fusion domain, a polyhistidine for $Ni^+$-affinity chromatography, a solubility sequence of approximately 5 kD, and an endopeptidase cleavage site which yields a full length MOMP with a modified amino terminal (as illustrated in FIG. 2) containing an alanine insert between the amino terminal methionine and the adjacent lysine. Either the full length expressed recombinant fusion protein or the modified MOMP following endopeptidase cleavage can be used as the antigen for a Chlamydia species ELISA. Other expression systems in E. coli or Baculovirus can be used for synthesis of the MOMP protein as the antigen in ELISA. The process is performed by non-covalent attachment of 50 ng recombinant MOMP in each well (rows 1–11) of a 96 well microtiter plate (Immulon 4) in carbonate buffer at pH 9.5 with an overnight incubation at 4° C. The plate is washed with PBS, 0.15% Tween20 x3 and is then blocked with PBS, 1% BSA, 0.15% Tween, 20 at 300 ml per well for 1 hour at RT and then washed x3 with PBS, 0.15% Tween20. Serum is serially diluted in PBS in triplicate in a separate plate and 50 µl of each well transferred to corresponding wells of a MOMP ligand plate, and the following sequence is followed: incubate at 37° C. for 1 hour using a parafilm or other suitable cover to prevent non-uniform evaporation. Wash with PBS, 1% FCS, 0.05% $NaN_3$ x5. Incubate each well with a predetermined dilution of biotin conjugated anti-human monoclonal IgG or monoclonal IgM. Incubate at 37° C. for 1 hour with cover. Wash (x3) with PBS, 1% FCS, 0.05% $NaN_3$. Follow with 50 µl strepavidin-alkaline phosphatase conjugate (1:200 in PBS, 1% BSA, 0.15% Tween20) for 1 hour at 37° C. with cover. Wash x3 with PBS, 1% CS (calf serum), 0.05% $NaN_3$. Color is developed with p-nitrophenyl phosphate in glycine buffer at pH 9.6. The color yield is measured on a microtiter colorimeter using a 405 nm filter. The end point titer is the highest dilution of serum or secretion yielding a color yield>3 SD over background (n=8). Analysis is simplified by computer-generated end point antibody titer or other antibody level measure identification and/or quantity of specific antibody (IgG, IgM, or total Ig) in the test sample using appropriate controls. Other strepavidin or avidin enzyme conjugates can be substituted such as strepavidin peroxidase or strepavidin-galactosidase with an approximate substitute yielding a detectable color for quantitation.

b. Peptide-Based ELISA

The recombinant MOMP-based ELISA described above provides a sensitive method for the quantitation of immunoglobulins against the Chlamydia genus in serum, plasma, CSF, and other body fluids. In order to provide ELISA assays that are species- and potentially strain-specific for the various Chlamydia, two regions in the MOMP have been identified which show minimal amino acid sequence homologies and which are predicted by computer analysis (Intelligenetics) to be excellent antigenic domains by virtue of hydrophilicity and mobility on the solvent-accessible surface of MOMP. FIG. 3 illustrates the constant and variable domain (VD) of the various chlamydial species. The identified species-specific antigenic domains are located in VD1 and VD2. FIG. 4 illustrates the peptide amino acid sequences employed for the construction of peptide based ELISAs with species specificity for VD1. FIG. 5 illustrates the peptides for VD2 which are used similarly to the VD1 sequences. ELISA methodology parallels that described above for the recombinant MOMP-based ELISA. In addition, a highly antigenic domain (FIG. 6) common to all Chlamydia has been identified and was developed as an alternative genus-specific ELISA for the Chlamydia. Immunization of rabbits has verified the antigenicity of each peptide to each peptide (Table 7). Monoclonal antibodies have further verified the specificities and antigenicity of each peptide (Table 7) as predicted by computer analysis of the nucleotide-generated amino acid sequence of each species-specific MOMP.

TABLE 7

Antigenic Responses To Peptides From 4 Species of Chlamydiae Identified By Hydrophilicity And Peptide Movement As Highly Antigenic

| Chlamydiae Species | Peptide[b] | Titer[a] Pre | Post |
|---|---|---|---|
| c. pneumoniae | 90–105 | 100 | >3200 |
| c. trachomatis L2 | 91–106 | 900 | >3200 |
| c. psittaci | 92–106 | 400 | >3200 |
| c. trachomatis (mouse) | 99–105 | 0 | >3200 |
| c. pneumoniae | 158–171 | 25 | >3200 |
| c. trachomatis L2 | 159–175 | 200 | >3200 |
| c. psittaci | 160–172 | 100 | >3200 |
| c. trachomatis (mouse) | 158–171 | 800 | >3200 |
| c. pneumoniae | 342–354 | 200 | >3200 |
| c. trachomatis L2 | 342–354 | 100 | >3200 |
| c. psittaci | ND[c] | | |
| c. trachomatis (mouse) | ND[c] | | |

[a]Reciprocal titer
[b]Immunogenic peptide and ELISA antigen of specific amino acid sequence against the indicated pre-immunization and post-itnmunization rabbit serum
[c]ND, not done Table 8 illustrates reciprocal titers of a polyclonal and monoclonal antibody against C. trachomatis cross-reactive against C. pneumoniae peptide encompassing amino acids 342–354 and a recombinant full length MOMP from C. pneumoniae.

TABLE 8

Reciprocal titers of a polyclonal and a monoclonal antibody against C. trachomatis cross-reactive against C. pneumoniae peptide encompassing amino acids 342–354 and a recombinant full length MOMP from C. pneumoniae

| Antigen | Titer[a] Polyclonal Ab[b] | Monoclonal Ab[c] |
|---|---|---|
| CPN Momp[d] | 400 | 0 |
| CPN 90–105[e] | 50 | 0 |
| CPN 158–171[f] | 50 | 0 |
| CPN 342–354[g] | >3200 | 1600 |

[a]Reciprocal titer
[b]Polyclonal goat Ab from Chemicon Inc. against MOMP of C. trachomatis
[c]Monoclonal Ab (ICN, Inc.) against MOMP of C. trachomatis
[d]C. pneumoniae recombinant MOMP
[e]Amino acid peptide 90–105 of C. pneumoniae
[f]Amino acid peptide 158–171 of C. pneumoniae
[g]Amino acid peptide 342–354 of C. pneumoniae Example 3

Detection Assay Methods (Diagnostic)

a. Immunoglobulin (Ig) assay

C. pneumoniae EBs were grown in primary human umbilical vein endothelial cells (HuEVEC; early passage), HeLa 199, or a suitable alternative in the presence of 1 µg/ml cycloheximide at 35° C. under 5% $CO_2$. Permissive cells were lysed at 3 days, thereby liberating EBs. The latter were harvested from infection flasks, sonicated, and cellular debris were removed after sonication by a low speed centrifugation (~600xg) for 5 minutes. EBs were pelleted by high speed centrifugation (30,000xg) for 30 minutes at 4° C. The EB pellet was washed with PBS x1 and was reconstituted in 2 ml PBS per four 25-cm² culture flask and sonicated at maximum power for 20 seconds and a 0.5 cycle time using a Braun-Sonic U sonicator. EB protein concentration was determined by the Bradford method and the sonicated infectious EB suspension was rendered non-infectious by the addition of 37% formaldehyde to a final 10% formaldehyde concentration with constant agitation during addition. Formalin-treated EBs were added to 96-well plates at 50 µl per well containing 50 ng EB (total of 5 µg/plate) and air dried. The plate was washed with PBS-0.15% Tween20 ×3 and was then blocked with PBS-1% BSA-0.15% Tween20 at 300 µl per well for 1 hour at room temperature and then washed ×3 with PBS-0.15% Tween20. Serum was serially diluted in PBS in duplicate in a separate plate and 50 µl of each well transferred to corresponding wells of a MOMP ligand plate and the following sequence was followed: incubate at 37° C. for 1 hour using a parafilm cover; wash with PBS-1% FCS-0.05% NaN3 ×5; incubate each well with a predetermined dilution of biotin-conjugated, antihuman monoclonal IgG or monoclonal IgM; incubate at 37° C. for 1 hour with cover; wash (×3) with PBS, 1% FCS, 0.05% NaN3; follow with 50 µl strepavidin-alkaline phosphatase conjugate (1:200 in PBS-1% BSA-0.15% Tween20) for 1 hour at 37° C. with cover; and wash ×3 with PBS, 1% CS, 0.05% NaN3. Color was developed with p-nitrophenyl phosphate in glycine buffer at pH 9.6. The color yield was measured on a Flow microtiter calorimeter using a 405 nm filter. End point titer was the highest dilution of serum or secretion yielding a color yield>3 SD over background (n=8).

b. Western blot

Western blots were prepared by SDS-PAGE of *C. pneumoniae* EBs (non-formalin fixed) harvested from infected HuEVEC or HeLa cell lysates, electrophoresed under standard SDS-PAGE conditions, and transferred to nitrocellulose achieved with an active diffusion transfer. Albumin-blocked strips were prepared from nitrocellulose sheets and incubated 1 hour with 1.2 ml of a 1:40 dilution of test serum. Detection was achieved with an alkaline phosphatase-conjugated, mouse anti-human antibody, and developed with 5-bromo-4-chloro-3'-indolyphosphate p-toluidine/nitro-blue tetrazolium chloride (BCIP/NBT, Pierce Chemical Company). Polyclonal animal anti-human antibodies can alternatively be used.

c. Antigen Capture Assay for Chlamydial MOMP

The peptides described in FIGS. 3–5 were conjugated via disulfide bonding to keyhole limpet hemocyanin (KLH) by standard methods (Bernatowicz et al., *Anal. Biochem.* 155 (1):95–102 (1986)). The peptide conjugates in alum were used to generate polyclonal and/or monoclonal antibodies to the species-specific domains of MOMP which is used as a capture antibody in 96 well microtiter plates. Final configuration can follow a number of alternative routes to yield quantitation of MOMP in body fluids. The favored configuration utilizes biotin labeled recombinant MOMP in a competition assay with strepavidin/alkaline phosphatase generated color development based on the quantity of biotinylated recombinant MOMP displaced by unlabeled MOMP in body fluids.

Example 4

In Vitro Antimicrobial Susceptibility Testing for *C. pneumoniae*

Tissue culture cells containing cryptic phase *C. pneumoniae* (H-292, HeLa, HEL, HuEVEC, McCoy, etc.) are plated at subconfluency in a 96-well microtiter plate (flasks or plates or other configurations can be alternatively used) and cultured in the presence of various antibiotics (singly and in combination) with the medium changed daily. Analysis of chlamydiacidal activity is carried out by assessing loss of solution PCR signal, or relative activity can be quantified by dilution titer of the starting material using the absence of PCR signal as the endpoint titer (i.e., last dilution to yield specific PCR signal).

Two week exposure of single agents including the fluoroquinolone, ofloxacin, and the macrolide, clarithromycin, at 1 μg/ml failed to clear HeLa cells in culture of a detectable PCR signal for the MOMP gene of *Chlamydia pneumoniae*. In contrast, triple agents consisting of isoniazid (INH), metronidazole, and penicillamine (1 μg/ml each) resulted in no detectable PCR signal (Table 9). None of these agents, effective in the triple combination, is currently recognized as an anti-chlamydial agent.

Table 10 provides the results of an expanded study of antimicrobial susceptibilities at two different concentrations of antimicrobial agents, used alone and in combination, when exposed to the antimicrobial agents for two weeks. In addition to the agents already mentioned, minocycline, doxycycline, rifampin and sulfamethoxizole/trimethoprim, at all concentrations tested, failed to clear the PCR signal for chlamydia MOMP. Only the triple combination of isoniazid, metronidazole and penicillamine cleared the PCR signal. The triple combination was effective at both low and high concentrations. Table 10 also demonstrates the effect of a 4 week exposure with the same expanded series of antimicrobial agents alone and in combination. A number of triple combinations of antimicrobial agents resulted in cell cultures in which the PCR signal for the chlamydial MOMP gene could not be detected.

TABLE 9

Susceptibility to Antibiotics for Cryptic Chlamydia pneumoniae Cultured in HeLa Cells[a]

| Antibiotic | Conc (μg/ml) | PCR[b] |
|---|---|---|
| Ofloxacin | 1 | positive |
| Clarithromycin | 1 | positive |
| INH | 1 | positive |
| Metronidazole | 1 | positive |
| Penicillamine | 1/1 | positive |
| INH + Metronidazole + Penicillamine | 1/1/4 | negative |
| Control | 0 | positive |

[a]Cultured in the presence of the indicated antibiotic(s), but with no cycloheximide. Media changes at 48–72 hours.
[b]Analysis following 2 week exposure to antimicrobial agents.

TABLE 10

Susceptibility to Antibiotics for Cryptic *Chlamydia pneumoniae* Cultured in HeLa Cells[a] by PCR

| Antibiotic | Conc (μg/ml) | PCR 2 week | PCR 4 week |
|---|---|---|---|
| Minocycline | 1 | pos | pos |
| Doxycycline | 1 | pos | pos |
| Isoniazide | 1 | pos | pos |
| TMP/SMZ[b] | 100 | pos | pos |
| Minocycline + Metronidazole + penicillamine | 1/1/4 | pos | pos |
| Doxycyclin + Metronidazole + penicillamine | 1/1/4 | pos | neg |
| Isoniazid + Metronidazole + penicillamine | 1/1/4 | neg | neg |
| TMP/SMZ + Metronidazole + peni- | 100/1/4 | pos | neg |

TABLE 10-continued

Susceptibility to Antibiotics for Cryptic
*Chlamydia pneumoniae* Cultured in HeLa Cells[a] by PCR

| Antibiotic | Conc (µg/ml) | PCR 2 week | PCR 4 week |
|---|---|---|---|
| cillamine | | | |
| Metronidazole | 0.25 | pos | pos |
| Clarithromycin | 0.25 | pos | pos |
| Rifampin | 0.25 | pos | pos |
| Ofloxacin | 0.25 | pos | pos |
| Minocycline | 0.25 | pos | pos |
| Doxycycline | 0.25 | pos | pos |
| TMP/SMZ + Metronidazole | 25/0.25 | pos | pos |
| Ofloxacin + Metronidazole | 0.25/0.25 | pos | pos |
| Rifampin + Metronidazole + penicillamine | 0.25/0.25/4 | pos | pos |
| Rifampin + Metronidazole + Ofloxacin | 0.25/0.25/0.25 | pos | pos |
| Clarithromycin + Metronidazole + penicillamine | 0.25/0.25/1 | pos | neg |
| Doxycycline + Metronidazole + penicillamine | 0.25/0.25/1 | pos | pos |
| Minocycline + Metronidazole + penicillamine | 0.25/0.25/1 | pos | neg |
| Isoniazid + Metronidazole + penicillamine | 0.25/0.25/1 | neg | neg |
| TMP/SMZ | 25 | pos | pos |
| Rifampin + Metronidazole | 0.25/0.25 | pos | pos |
| None | 0 | pos | pos |

[a]Cultured in the presence of the indicated antibiotics, but with no cycloheximide. Media changes at 48–72 hours. pos = positive, neg = negative
[b]TMP/SMZ = trimethoprim/sulfamethoxazole

Response to Antibiotic Therapy

Table 11 illustrates typical responses to combination antibiotic therapy in a variety of patients with diagnostic evidence of an active infection by *C. pneumoniae*. Unlike typical immune responses to infection with infectious agents, most of the included patients have not only detectable IgM titers against the chlamydial genus but in many cases very high IgM titers. With specific therapy over time the IgM titers generally fall, with a rise in IgG titer (as expected). Correct methods of defecting antibodies against *C. pneumoniae* (Indirect immunofluoresence, IMF) are incapable of accurately identifying high ISM titers against *C. pneumoniae*. Moreover, current procedures are genus specific and not species specific as are peptide-based ELISAs. With clearing of the pathogen, the IgG titers fall. Concomitant with combination antibiotic therapy, there is generally an improvement of patient symptoms associated with the specific diagnosis indicative of evidence of an active chlamydial infection.

TABLE 11

Serological and PCR Responses to Combination Antibiotic Therapy

| Patient | Diagnosis[a] | Titer IgM | Titer IgG | Months of Combination Antibiotic Therapy | PCR | Status |
|---|---|---|---|---|---|---|
| PH | FM | 800 | 800 | 6 months | + | Asymptomatic |
| | | 3200 | 1600 | | + | |
| | | 800 | 200 | | wk+ | |
| BL | MS | 2000 | 500 | 9 months | + | Dramatic |
| | | 400 | 3200 | 9 months | wk+ | Improvement: |
| MM | CFS/AND | 3200 | 800 | 1 month | + | Improvement; |
| | | 400 | 1600 | | + | Relapse (non-compliant) |
| PM | CFS | 2000 | 25 | 6 months | + | Asymptomatic |
| | | 400 | 800 | | wk+ | |
| AM | IBD | 800 | 0 | 6 months | wk+ | 90% |
| | | 3200 | 400 | | + | Improvement |
| FO | MS | 800 | 3200 | 10 months | st+ | Improvement |
| | | 800 | 800 | | + | in speeds and |
| | | 400 | 600 | | wk+ | bowl continence |
| | | 400 | 800 | | + | |
| WM | CF | 25 | 25 | Pre-illness | wk+ | Asymptomatic |
| | | 1000 | 25 | serum <-- | st+ | |
| | | 50 | 800 | Antibiotics | + | |
| | | 50 | 1600 | start | wk+ | |
| | | 50 | 400 | | - | |
| HM | CF | 2000 | 100 | 6 months | + | Asymptomatic |
| | | 3200 | 3200 | | + | |
| | | 200 | 800 | | wk+ | |
| CN | CFS | 3200 | 800 | 8 months | + | 75% |
| | | 800 | 800 | | wk+ | Improvement |
| AN | MS/CFS | 400 | 400 | | wk+ | Strength ↑ |
| | | 200 | 3200 | | st+ | Fatigue ↓ |
| JS | CFS (severe) | 2000 | 2000 | 5 months | st+ | Asymptomatic |
| | | 2000 | 2000 | | + | |
| | | 200 | 800 | | - | |
| AG | IBD | 3200 | 400 | 9 months | + | Improvement |
| | | 800 | 400 | | + | in joint Sx |
| | | 800 | 800 | | + | |
| | | 800 | 400 | | - | |
| AT | CF | 3200 | 3200 | 9 months | + | Asymptomatic |
| | | 1600 | 1600 | | + | |
| | | 1600 | 1600 | | + | |
| | | 800 | 800 | | + | |
| | | 400 | 400 | | + | |
| LH | RA | 3200 | 1600 | 6 months | wk+ | Improvement |
| | | 600 | 400 | | wk+ | |
| | | 200 | 50 | | + | |
| HS | MS | 2000 | 400 | 5 months | + | Improvement |
| | | 3200 | 800 | | + | |
| | | 50 | 200 | | - | |
| ST | CFS/FM | >1000 | 100 | 7 months | wk+ | Asymptomatic |
| | | 1000 | 100 | | wk+ | |
| | | 400 | 100 | | + | |
| | | 800 | 3200 | | + | |
| | | 100 | 100 | | + | |
| RV | CF | 1000 | 100 | 10 months | + | Asymptomatic |
| | | 400 | 1600 | | + | |
| | | 400 | 400 | | - | |

[a]CF = Chronic Fatigue < 6 months
CFS = Chronic Fatigue Syndrome
FM = Fibromyalgia
IBD = Inflammatory Bowel Disease
MS = Multiple Sclerosis
AND = Autonomic nervous dysfunction (neural-mediated hypotension)
RA = Rheumatoid Arthritis
IgM >> IgG → immune tolerance to the antigen
IgG >> IgM → successful immune control of the antigen Although the foregoing description is directed toward Chlamydia, it is merely for exemplary purposes and is not intended to limit the invention thereto. The invention therefore is relevant for other to obligate intracellular pathogens. For example, pathogens that must be in an intracellular location in order to replicate, include but are not limited to prions, viruses, Chlamydiae spp., Mycoplasma spp., Ehrilichia spp., Rickettsia spp., Bartinella spp., Borrelia spp., *Toxoplasma gondii*, Leishmania spp. and Trypanosomes (e.g., Malaria). Additionally, included are pathogens that are able to survive in an intracellular location and can find a physiologic advantage to do so, for example, Legionella spp., Salmonella spp., Listeria spp., Histoplasma spp., Yersinia spp. and Mycobacteria spp. Intracellular pathogens that are able to utilize selective intracellular locations to enhance survivability and/or pathogenics, are embraced in this invention and include but are not limited to Neisseria spp., Staphylococcus spp., Hemophilus spp., *Escherichia coli*, Candida spp. and Torulopsis spp., Equivalents While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method of detecting Chlamydia in a sample, said method comprising:
   (a) providing an antibody that specifically binds to a peptide having a sequence consisting essentially of SEQ ID NO: 97; and
   (b) performing on a sample an antigen capture assay using said antibody wherein binding of said antibody indicates the presence of Chlamydia in said sample.

2. A method for detecting Chlamydia in a sample, said method comprising the steps of:
   a) providing a sample;
   b) contacting said sample with a peptide having a sequence consisting essentially of SEQ ID NO: 97; and
   c) detecting the binding of an antibody in said sample to said peptide, wherein binding of said antibody to said peptide indicates the presence of Chlamydia in said sample.

3. The method of claim 2, wherein said antibody specifically binds to a peptide having a sequence consisting essentially of SEQ ID NO: 97, and the binding of said antibody to said peptide indicates that said Chlamydia is *Chlamydia pneumoniae*.

4. A method for detecting the presence of Chlamydia in a sample, said method comprising the steps of:
   a) immobilizing a sample onto a substrate;
   b) providing an antibody that specifically binds to a peptide having a sequence consisting essentially of SEQ ID NO: 97;
   c) contacting said immobilized sample with said antibody wherein said antibody becomes immobilized if said sample contains Chlamydia; and
   d) detecting the presence of immobilized antibody, wherein the presence of immobilized antibody indicates the presence of Chlamydia in said sample.

5. The method of claim 4, wherein said antibody specifically binds to a peptide having a sequence consisting essentially of SEQ ID NO: 97, and the presence of immobilized antibody indicates that said Chlamydia is *Chlamydia pneumoniae*.

* * * * *

UNITED STATES PATENT AND TRADEMARK OFFICE
CERTIFICATE OF CORRECTION

PATENT NO.       : 6,838,552 B1
APPLICATION NO.  : 09/709201
DATED            : January 4, 2005
INVENTOR(S)      : William M. Mitchell et al.

It is certified that error appears in the above-identified patent and that said Letters Patent is hereby corrected as shown below:

Column 4,
Line 64, replace "treatinq" with -- treating --.

Column 5,
Line 52, replace "HuEVEC-CP" with -- HuEVEC-CF --.

Column 21,
Lines 6 and 12, replace "EBB" with -- EBs --.

Column 23,
Line 24, replace "(IC)" with -- (IC), --; and
Line 28, replace "investigation correlation" with -- investigation. Correlation --.

Column 30,
Line 25, replace "as." with -- as --.

Column 32,
Line 63, replace "(Novagen. Inc.)" with -- (Novagen, Inc.) --.

Column 33,
Line 32, replace "yield>3" with -- yield >3 --.

Column 34,
Line 23, replace "post-itnmunization" with -- post-immunization --.

UNITED STATES PATENT AND TRADEMARK OFFICE
CERTIFICATE OF CORRECTION

PATENT NO. : 6,838,552 B1
APPLICATION NO. : 09/709201
DATED : January 4, 2005
INVENTOR(S) : William M. Mitchell et al.

It is certified that error appears in the above-identified patent and that said Letters Patent is hereby corrected as shown below:

Column 35,
Line 26, replace "calorimeter" with -- colorimeter --; and
Line 28, replace "yield>3" with -- yield >3 --.

Column 36,
Line 24, replace "chlamydia" with -- chlamydial --.

Signed and Sealed this

Twenty-seventh Day of June, 2006

JON W. DUDAS
*Director of the United States Patent and Trademark Office*

SEQUENCE LISTING

```
<160> NUMBER OF SEQ ID NOS: 114

<210> SEQ ID NO 1
<211> LENGTH: 50
<212> TYPE: DNA
<213> ORGANISM: Homo sapiens

<400> SEQUENCE: 1
atgaaaaaac tcttaaagtc ggcgttatta tccgccgcat ttgctggttc          50

<210> SEQ ID NO 2
<211> LENGTH: 50
<212> TYPE: DNA
<213> ORGANISM: Homo sapiens

<400> SEQUENCE: 2
atgaaaaaac tcttaaagtc ggcgttatta tccgccgcat ttgctggttc          50

<210> SEQ ID NO 3
<211> LENGTH: 50
<212> TYPE: DNA
<213> ORGANISM: Homo sapiens

<400> SEQUENCE: 3
atgaaaaaac tcttgaagtc ggcattattg tttgccgcta cgggttccgc          50

<210> SEQ ID NO 4
<211> LENGTH: 50
<212> TYPE: DNA
<213> ORGANISM: Homo sapiens

<400> SEQUENCE: 4
atgaaaaaac tcttaaagtc ggcgttatta tccgccgcat ttgctggttc          50

<210> SEQ ID NO 5
<211> LENGTH: 50
<212> TYPE: DNA
<213> ORGANISM: Homo sapiens

<400> SEQUENCE: 5
atgaaaaaac tcttgaaatc ggcattattg tttgccgcta cgggttccgc          50

<210> SEQ ID NO 6
<211> LENGTH: 50
<212> TYPE: DNA
<213> ORGANISM: Homo sapiens
```

-continued

```
<400> SEQUENCE: 6
atgaaaaaac tcttgaaatc ggcattattg tttgccgcta cgggttccgc          50

<210> SEQ ID NO 7
<211> LENGTH: 50
<212> TYPE: DNA
<213> ORGANISM: Homo sapiens

<400> SEQUENCE: 7
atgaaaaaac tcttgaaatc ggcattattg tttgccgcta cgggttccgc          50

<210> SEQ ID NO 8
<211> LENGTH: 50
<212> TYPE: DNA
<213> ORGANISM: Homo sapiens

<400> SEQUENCE: 8
atgaaaaaac tcttgaaatc ggcattatta tttgccgcta cgggttccgc          50

<210> SEQ ID NO 9
<211> LENGTH: 50
<212> TYPE: DNA
<213> ORGANISM: Homo sapiens

<400> SEQUENCE: 9
atgaaaaaac tcttaaaatc ggcattatta tttgccgctg cgggttccgc          50

<210> SEQ ID NO 10
<211> LENGTH: 50
<212> TYPE: DNA
<213> ORGANISM: Homo sapiens

<400> SEQUENCE: 10
atgaaaaaac tcttgaaatc ggtattagta tttgccgctt tgagttctgc          50

<210> SEQ ID NO 11
<211> LENGTH: 50
<212> TYPE: DNA
<213> ORGANISM: Homo sapiens

<400> SEQUENCE: 11
atgaaaaaac tcttgaaatc ggtattagta tttgccgctt tgagttctgc          50

<210> SEQ ID NO 12
<211> LENGTH: 50
<212> TYPE: DNA
<213> ORGANISM: Homo sapiens

<400> SEQUENCE: 12
atgaaaaaac tcttgaaatc ggtattagta tttgccgctt tgagttctgc          50

<210> SEQ ID NO 13
<211> LENGTH: 50
<212> TYPE: DNA
<213> ORGANISM: Homo sapiens

<400> SEQUENCE: 13
atgaaaaaac tcttgaaatc ggtattagta tttgccgctt tgagttctgc          50

<210> SEQ ID NO 14
<211> LENGTH: 50
<212> TYPE: DNA
```

```
<400> SEQUENCE: 14
atgaaaaaac tcttgaaatc ggtattagta tttgccgctt tgagttctgc          50

<210> SEQ ID NO 15
<211> LENGTH: 50
<212> TYPE: DNA
<213> ORGANISM: Homo sapiens

<400> SEQUENCE: 15
atgaaaaaac tcttgaaatc ggtattagta tttgccgctt tgagttctgc          50

<210> SEQ ID NO 16
<211> LENGTH: 50
<212> TYPE: DNA
<213> ORGANISM: Homo sapiens

<400> SEQUENCE: 16
atgaaaaaac tcttgaaatc ggtattagtg tttgccgctt tgagttctgc          50

<210> SEQ ID NO 17
<211> LENGTH: 50
<212> TYPE: DNA
<213> ORGANISM: Homo sapiens

<400> SEQUENCE: 17
atgaaaaaac tcttgaaatc ggtattagtg tttgccgctt tgagttctgc          50

<210> SEQ ID NO 18
<211> LENGTH: 50
<212> TYPE: DNA
<213> ORGANISM: Homo sapiens

<400> SEQUENCE: 18
atgaaaaaac tcttgaaatc ggtattagtg tttgccgctt tgagttctgc          50

<210> SEQ ID NO 19
<211> LENGTH: 50
<212> TYPE: DNA
<213> ORGANISM: Homo sapiens

<400> SEQUENCE: 19
atgaaaaaac tcttgaaatc ggtattagca tttgccgttt tgggttctgc          50

<210> SEQ ID NO 20
<211> LENGTH: 50
<212> TYPE: DNA
<213> ORGANISM: Homo sapiens

<400> SEQUENCE: 20
gtttaattaa cgagagagct gctcacgtat ctggtcagtt cagattctaa          50

<210> SEQ ID NO 21
<211> LENGTH: 50
<212> TYPE: DNA
<213> ORGANISM: Homo sapiens

<400> SEQUENCE: 21
gtttaattaa cgagagagct gctcacgtat ctggtcagtt cagattctaa          50

<210> SEQ ID NO 22
<211> LENGTH: 50
<212> TYPE: DNA
```

<213> ORGANISM: Homo sapiens

<400> SEQUENCE: 22
caacgttaat cgacgctgac aaatggtcaa tcactggtga agcacgctta          50

<210> SEQ ID NO 23
<211> LENGTH: 50
<212> TYPE: DNA
<213> ORGANISM: Homo sapiens

<400> SEQUENCE: 23
gtttaattaa cgagagagct gctcacatat ctggtcagtt cagattctaa          50

<210> SEQ ID NO 24
<211> LENGTH: 50
<212> TYPE: DNA
<213> ORGANISM: Homo sapiens

<400> SEQUENCE: 24
aacgttaatc gacgctgaca aatggtcaat cactggtgaa gcacgcttaa          50

<210> SEQ ID NO 25
<211> LENGTH: 50
<212> TYPE: DNA
<213> ORGANISM: Homo sapiens

<400> SEQUENCE: 25
aacgttaatc gacgctgaca aatggtcaat cactggtgaa gcacgcttaa          50

<210> SEQ ID NO 26
<211> LENGTH: 50
<212> TYPE: DNA
<213> ORGANISM: Homo sapiens

<400> SEQUENCE: 26
gcttaatcaa tgaaagagcc gctcacatga atgctcaatt cagattctaa          50

<210> SEQ ID NO 27
<211> LENGTH: 50
<212> TYPE: DNA
<213> ORGANISM: Homo sapiens

<400> SEQUENCE: 27
gcttaatcaa tgaaagagct gctcacatga atgctcaatt cagattctaa          50

<210> SEQ ID NO 28
<211> LENGTH: 50
<212> TYPE: DNA
<213> ORGANISM: Homo sapiens

<400> SEQUENCE: 28
gcttaatcga cgaaagagct gctcacatta atgctcaatt cagattctaa          50

<210> SEQ ID NO 29
<211> LENGTH: 50
<212> TYPE: DNA
<213> ORGANISM: Homo sapiens

<400> SEQUENCE: 29
cgcagttaca gttgagactc gcttgatcga tgagagagca gctcacgtaa          50

<210> SEQ ID NO 30
<211> LENGTH: 50

-continued

<212> TYPE: DNA
<213> ORGANISM: Homo sapiens

<400> SEQUENCE: 30
gcttgatcga tgagagagca ggtcacgtaa atgcacaatt ccggttctaa         50

<210> SEQ ID NO 31
<211> LENGTH: 50
<212> TYPE: DNA
<213> ORGANISM: Homo sapiens

<400> SEQUENCE: 31
gcttgatcga tgagagagca gctcacgtaa atgcacaatt ccgcttctaa         50

<210> SEQ ID NO 32
<211> LENGTH: 50
<212> TYPE: DNA
<213> ORGANISM: Homo sapiens

<400> SEQUENCE: 32
cgcttgatcg atgagagact gctcacgtaa atgcacaatt ccgcttctaa         50

<210> SEQ ID NO 33
<211> LENGTH: 50
<212> TYPE: DNA
<213> ORGANISM: Homo sapiens

<400> SEQUENCE: 33
gcttgatcga tgagagagct gctcacgtaa atgcacaatt ccgcttctaa         50

<210> SEQ ID NO 34
<211> LENGTH: 50
<212> TYPE: DNA
<213> ORGANISM: Homo sapiens

<400> SEQUENCE: 34
gcttgatcga tgagagagca gctcacgtaa atgcacaatt ccgcttctaa         50

<210> SEQ ID NO 35
<211> LENGTH: 50
<212> TYPE: DNA
<213> ORGANISM: Homo sapiens

<400> SEQUENCE: 35
gcttgatcga tgagagagct gctcacgtaa atgcacaatt ccgcttctaa         50

<210> SEQ ID NO 36
<211> LENGTH: 49
<212> TYPE: DNA
<213> ORGANISM: Homo sapiens

<400> SEQUENCE: 36
cttgatcgat gagagagctg ctcacgtaaa tgcacaattc cgcttctaa          49

<210> SEQ ID NO 37
<211> LENGTH: 50
<212> TYPE: DNA
<213> ORGANISM: Homo sapiens

<400> SEQUENCE: 37
gcttgatcga tgagagagca gctcacgtaa atgcacaatt ccgcttctaa         50

<210> SEQ ID NO 38

```
<211> LENGTH: 50
<212> TYPE: DNA
<213> ORGANISM: Homo sapiens

<400> SEQUENCE: 38
gcttgatcga tgaaagagca gctcacgtaa atgctcagtt ccgtttctaa            50

<210> SEQ ID NO 39
<211> LENGTH: 22
<212> TYPE: DNA
<213> ORGANISM: Homo sapiens

<400> SEQUENCE: 39
cagatacgtg agcagctctc tc                                         22

<210> SEQ ID NO 40
<211> LENGTH: 25
<212> TYPE: DNA
<213> ORGANISM: Homo sapiens

<400> SEQUENCE: 40
ctcttaaagt cggcgttatt atccg                                      25

<210> SEQ ID NO 41
<211> LENGTH: 38
<212> TYPE: DNA
<213> ORGANISM: Homo sapiens

<400> SEQUENCE: 41
atgaaaaaac tcttaaagtc ggcgttatta tccgccgc                        38

<210> SEQ ID NO 42
<211> LENGTH: 40
<212> TYPE: DNA
<213> ORGANISM: Homo sapiens

<400> SEQUENCE: 42
ttagaatctg aactgaccag atacgtgagc agctctctcg                      40

<210> SEQ ID NO 43
<211> LENGTH: 45
<212> TYPE: DNA
<213> ORGANISM: Homo sapiens

<400> SEQUENCE: 43
agcttaccat ggctaaaaaa ctcttaaagt cggcgttatt atccg                 45

<210> SEQ ID NO 44
<211> LENGTH: 39
<212> TYPE: DNA
<213> ORGANISM: Homo sapiens

<400> SEQUENCE: 44
atatgcggcc gctcatagaa tctgaactga ccagatacg                       39

<210> SEQ ID NO 45
<211> LENGTH: 100
<212> TYPE: PRT
<213> ORGANISM: Homo sapiens

<400> SEQUENCE: 45

Met Lys Lys Leu Leu Lys Ser Val Leu Val Phe Ala Ala Leu Ser Ser
 1               5                  10                  15
```

```
Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Gln Thr Asp Val Asn Lys
65                  70                  75                  80

Glu Phe Gln Met Gly Ala Lys Pro Thr Thr Ala Thr Gly Asn Ala Ala
            85                  90                  95

Ala Pro Ser Thr
            100

<210> SEQ ID NO 46
<211> LENGTH: 100
<212> TYPE: PRT
<213> ORGANISM: Homo sapiens

<400> SEQUENCE: 46

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
            35                  40                  45

Asp Pro Cys Thr Thr Trp Cys Asp Ala Ile Ser Met Ile Met Gly Tyr
        50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Thr Thr Gly Asn Ala Ala
            85                  90                  95

Ala Pro Ser Thr
            100

<210> SEQ ID NO 47
<211> LENGTH: 100
<212> TYPE: PRT
<213> ORGANISM: Homo sapiens

<400> SEQUENCE: 47

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
            35                  40                  45

Asp Pro Cys Thr Thr Trp Cys Asp Ala Ile Ser Met Arg Met Gly Tyr
        50                  55                  60

Tyr Gly Asp Phe Val Phe Asp Arg Val Leu Glu Thr Asp Val Asn Lys
65                  70                  75                  80

Glu Phe His Met Gly Ala Lys Pro Thr Thr Asp Thr Gly Asn Ser Ala
            85                  90                  95

Ala Pro Leu Thr
            100

<210> SEQ ID NO 48
<211> LENGTH: 100
```

```
<212> TYPE: PRT
<213> ORGANISM: Homo sapiens

<400> SEQUENCE: 48

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Thr Thr Trp Cys Asp Ala Ile Ser Met Ile Met Gly Tyr
    50                  55                  60

Tyr Gly Asp Phe Val Phe Asp Arg Val Leu Lys Thr Asp Val Asn Lys
65                  70                  75                  80

Glu Phe His Met Gly Asp Lys Pro Thr Ser Thr Thr Gly Asn Ala Thr
                85                  90                  95

Ala Pro Thr Thr
            100

<210> SEQ ID NO 49
<211> LENGTH: 100
<212> TYPE: PRT
<213> ORGANISM: Homo sapiens

<400> SEQUENCE: 49

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Thr Thr Trp Cys Asp Ala Ile Ser Met Ile Met Gly Tyr
    50                  55                  60

Tyr Gly Asp Phe Val Phe Asp Arg Val Leu Lys Thr Asp Val Asn Lys
65                  70                  75                  80

Glu Phe His Met Gly Asp Lys Pro Thr Ala Thr Thr Gly Asn Ala Ala
                85                  90                  95

Ala Pro Ser Thr
            100

<210> SEQ ID NO 50
<211> LENGTH: 101
<212> TYPE: PRT
<213> ORGANISM: Homo sapiens

<400> SEQUENCE: 50

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Thr Thr Trp Cys Asp Ala Ile Ser Met Ile Met Gly Tyr
    50                  55                  60

Tyr Gly Asp Phe Val Phe Asp Arg Val Leu Lys Thr Asp Val Asn Lys
65                  70                  75                  80

Glu Phe Lys Met Gly Glu Ala Leu Ala Gly Ser Thr Gly Asn Thr Thr
```

-continued

```
                85                  90                  95

Ser Thr Leu Ser Lys
            100

<210> SEQ ID NO 51
<211> LENGTH: 103
<212> TYPE: PRT
<213> ORGANISM: Homo sapiens

<400> SEQUENCE: 51

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Val Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Ala Gly
                85                  90                  95

Leu Gln Asn Asp Pro Thr Ile
            100

<210> SEQ ID NO 52
<211> LENGTH: 102
<212> TYPE: PRT
<213> ORGANISM: Homo sapiens

<400> SEQUENCE: 52

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Arg Asp Val Ala Gly Leu
                85                  90                  95

Glu Lys Asp Pro Val Val
            100

<210> SEQ ID NO 53
<211> LENGTH: 97
<212> TYPE: PRT
<213> ORGANISM: Homo sapiens

<400> SEQUENCE: 53

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45
```

```
Ala Pro Cys Thr Thr Trp Cys Asp Ala Ile Ser Met Val Met Gly Tyr
        50                  55                  60

Tyr Gly Asp Phe Val Phe Asp Arg Val Leu Lys Thr Asp Val Asn Lys
 65                  70                  75                  80

Glu Phe Gln Met Gly Ala Ala Pro Thr Thr Asn Asp Ala Ala Pro Lys
                 85                  90                  95

Thr

<210> SEQ ID NO 54
<211> LENGTH: 102
<212> TYPE: PRT
<213> ORGANISM: Homo sapiens

<400> SEQUENCE: 54

Met Lys Lys Leu Leu Lys Ser Val Leu Val Phe Ala Ala Leu Ser Ser
  1               5                  10                  15

Ala Ser Ser Leu Gln Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Thr Thr Trp Cys Asp Ala Ile Ser Met Val Met Gly Tyr
        50                  55                  60

Tyr Gly Asp Phe Val Phe Asp Arg Val Leu Lys Thr Asp Val Asn Lys
 65                  70                  75                  80

Glu Phe Gln Met Gly Ala Glu Pro Thr Thr Ser Asp Thr Ala Gly Leu
                 85                  90                  95

Ser Asn Asp Pro Thr Thr
            100

<210> SEQ ID NO 55
<211> LENGTH: 100
<212> TYPE: PRT
<213> ORGANISM: Homo sapiens

<400> SEQUENCE: 55

Met Lys Lys Leu Leu Lys Ser Val Ala Val Phe Val Ala Gly Ser Ser
  1               5                  10                  15

Ala Ser Ser Leu His Ala Leu Pro Val Gly Asn Pro Ala Glu Pro Ser
                 20                  25                  30

Leu Met Ile Asp Gly Ile Leu Trp Glu Gly Phe Gly Gly Asp Pro Cys
             35                  40                  45

Asp Pro Cys Thr Thr Trp Cys Asp Ala Ile Ser Met Arg Met Gly Leu
        50                  55                  60

Tyr Leu Asp Phe Val Phe Asp Arg Val Leu Lys Thr Asp Val Asn Lys
 65                  70                  75                  80

Gln Phe Glu Met Gly Ala Ala Pro Thr Gly Asp Ala Asp Leu Thr Thr
                 85                  90                  95

Ala Pro Thr Pro
            100

<210> SEQ ID NO 56
<211> LENGTH: 99
<212> TYPE: PRT
<213> ORGANISM: Homo sapiens

<400> SEQUENCE: 56

Met Lys Lys Leu Leu Lys Ala Val Leu Ala Phe Ala Phe Ala Gly Ser
```

-continued

```
              1               5              10              15
         Val Gly Ser Leu Gln Ala Leu Pro Val Gly Asn Pro Ala Ser Asp Ser
                         20                  25                  30

Leu Leu Ile Asp Gly Thr Ile Trp Glu Gly Ala Ala Gly Asp Pro Cys
                         35                  40                  45

Asp Pro Ala Thr Thr Trp Cys Asp Ala Ile Ser Leu Arg Ala Gly Phe
                         50                  55                  60

Tyr Gly Asp Phe Val Tyr Asp Ile Val Leu Lys Val Asp Ala Pro Lys
          65                  70                  75                  80

Thr Phe Ser Met Gly Ala Lys Pro Thr Thr Gly Asn Gly Ser Ala
                             85                  90                  95

Ala Ala Asn

<210> SEQ ID NO 57
<211> LENGTH: 100
<212> TYPE: PRT
<213> ORGANISM: Homo sapiens

<400> SEQUENCE: 57

Cys Thr Ala Arg Glu Asn Pro Ala Tyr Gly Arg His Met Gln Asp Ala
          1               5                  10                  15

Glu Met Phe Thr Asn Ala Ala Tyr Met Ala Leu Ile Asn Trp Asp Arg
                         20                  25                  30

Phe Asp Val Phe Cys Thr Leu Gly Ala Thr Ser Gly Tyr Leu Lys Gly
                         35                  40                  45

Asn Ser Ala Ser Phe Asn Leu Val Gly Leu Phe Gly Asp Asn Glu Asn
                         50                  55                  60

His Ala Thr Val Ser Asp Ser Lys Leu Val Pro Asn Met Ser Leu Asp
          65                  70                  75                  80

Gln Ser Val Val Glu Leu Tyr Thr Asp Thr Thr Phe Ala Trp Ser Ala
                             85                  90                  95

Gly Ala Arg Ala
                     100

<210> SEQ ID NO 58
<211> LENGTH: 65
<212> TYPE: PRT
<213> ORGANISM: Homo spiens

<400> SEQUENCE: 58

Leu Thr Ala Arg Glu Asn Pro Ala Tyr Gly Arg His Met Gln Asp Ala
          1               5                  10                  15

Glu Met Phe Thr Asn Cys Ala Tyr Met Ala Leu Ile Asn Trp Asp Arg
                         20                  25                  30

Phe Asp Val Phe Cys Thr Leu Gly Ala Ser Ser Gly Tyr Leu Lys Gly
                         35                  40                  45

Asn Ser Ala Ser Phe Asn Leu Val Gly Leu Phe Gly Asn Asn Glu Asn
                         50                  55                  60

Gln
          65

<210> SEQ ID NO 59
<211> LENGTH: 134
<212> TYPE: PRT
<213> ORGANISM: Homo sapiens

<400> SEQUENCE: 59
```

```
Cys Thr Ala Arg Glu Asn Pro Ala Tyr Gly Arg His Met Gln Asp Ala
  1               5                  10                  15

Glu Met Phe Thr Asn Cys Ala Tyr Met Ala Leu Ile Asn Trp Asp Arg
             20                  25                  30

Phe Asp Val Phe Cys Thr Leu Gly Ala Thr Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Lys Thr Val Lys Ala Glu Ser Val Pro Asn Met Ser Phe Asp Gln
 65                  70                  75                  80

Ser Val Val Glu Leu Tyr Thr Asp Thr Phe Ala Trp Ser Val Gly
                 85                  90                  95

Ala Arg Ala Thr Lys Val Ser Asn Gly Thr Phe Val Pro Asn Met Ser
             100                 105                 110

Leu Asp Gln Ser Val Val Glu Leu Tyr Thr Asp Thr Ala Phe Ala Trp
             115                 120                 125

Ser Val Gly Ala Arg Ala
             130
```

<210> SEQ ID NO 60
<211> LENGTH: 99
<212> TYPE: PRT
<213> ORGANISM: Homo sapiens

<400> SEQUENCE: 60

```
Leu Thr Ala Arg Glu Asn Pro Ala Tyr Gly Arg His Met Gln Asp Ala
  1               5                  10                  15

Glu Met Phe Thr Asn Cys Ala Tyr Met Ala Leu Ile Asn Trp Asp Arg
             20                  25                  30

Phe Asp Val Phe Cys Thr Leu Gly Ala Ser Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Ser Thr Val Lys Thr Asn Ser Val Pro Asn Met Ser Leu Asp Gln
 65                  70                  75                  80

Ser Val Val Glu Leu Tyr Thr Asp Thr Ala Phe Ser Trp Ser Val Gly
                 85                  90                  95

Ala Arg Ala
```

<210> SEQ ID NO 61
<211> LENGTH: 99
<212> TYPE: PRT
<213> ORGANISM: Homo sapiens

<400> SEQUENCE: 61

```
Cys Thr Ala Arg Glu Asn Pro Ala Tyr Gly Arg His Met Gln Asp Ala
  1               5                  10                  15

Glu Met Phe Thr Asn Ala Ala Tyr Met Ala Leu Ile Asn Trp Asp Arg
             20                  25                  30

Phe Asp Val Phe Cys Thr Leu Gly Ala Thr Ser Gly Tyr Leu Lys Gly
         35                  40                  45

Asn Ser Ala Ser Phe Asn Leu Val Gly Leu Phe Gly Asp Asn Glu Asn
     50                  55                  60

Gln Ser Thr Val Lys Lys Asp Ala Val Pro Asn Met Ser Phe Asp Gln
 65                  70                  75                  80

Ser Val Val Glu Leu Tyr Thr Asp Thr Thr Phe Ala Trp Ser Val Gly
```

-continued

```
                    85                  90                  95

Ala Arg Ala

<210> SEQ ID NO 62
<211> LENGTH: 99
<212> TYPE: PRT
<213> ORGANISM: Homo sapiens

<400> SEQUENCE: 62

Leu Val Glu Arg Thr Asn Pro Ala Tyr Gly Lys His Met Gln Asp Ala
  1               5                  10                  15

Glu Met Phe Thr Asn Cys Ala Tyr Thr Ala Leu Ile Asn Trp Asp Arg
                 20                  25                  30

Phe Asp Val Phe Cys Thr Leu Gly Ala Thr Ser Gly Tyr Leu Lys Gly
             35                  40                  45

Asn Ser Ala Ser Phe Asn Leu Val Gly Leu Phe Gly Asp Gly Val Asn
         50                  55                  60

Ala Thr Lys Pro Ala Ala Asp Ser Ile Pro Asn Val Gln Leu Asn Gln
 65                  70                  75                  80

Ser Val Val Glu Leu Tyr Thr Asp Thr Phe Ala Trp Ser Val Gly
                 85                  90                  95

Ala Arg Ala

<210> SEQ ID NO 63
<211> LENGTH: 100
<212> TYPE: PRT
<213> ORGANISM: Homo sapiens

<400> SEQUENCE: 63

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
                 20                  25                  30

Phe Asp Val Phe Cys Thr Leu Gly Ala Thr Thr Gly Tyr Leu Lys Gly
             35                  40                  45

Asn Ser Ala Ser Phe Asn Leu Val Gly Leu Phe Gly Thr Lys Thr Gln
         50                  55                  60

Ser Ser Ser Phe Asn Thr Ala Lys Leu Ile Pro Asn Thr Ala Leu Asp
 65                  70                  75                  80

Gln Ser Val Val Glu Leu Tyr Ile Asn Thr Thr Phe Ala Trp Ser Val
                 85                  90                  95

Gly Ala Arg Ala
            100

<210> SEQ ID NO 64
<211> LENGTH: 100
<212> TYPE: PRT
<213> ORGANISM: Homo sapiens

<400> SEQUENCE: 64

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
                 20                  25                  30

Phe Asp Val Phe Cys Thr Leu Gly Ala Thr Thr Gly Tyr Leu Lys Gly
             35                  40                  45

Asn Ser Ala Ser Phe Asn Leu Val Gly Leu Phe Gly Thr Lys Thr Gln
```

```
                    50                  55                  60
Ser Ser Gly Phe Asp Thr Ala Asn Ile Val Pro Asn Thr Ala Leu Asn
 65                  70                  75                  80

Gln Ala Val Val Glu Leu Tyr Thr Asp Thr Thr Phe Ala Trp Ser Val
                     85                  90                  95

Gly Ala Arg Ala
            100

<210> SEQ ID NO 65
<211> LENGTH: 100
<212> TYPE: PRT
<213> ORGANISM: Homo sapiens

<400> SEQUENCE: 65

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
                 20                  25                  30

Phe Asp Val Phe Cys Thr Leu Gly Ala Thr Thr Gly Tyr Leu Lys Gly
             35                  40                  45

Asn Ser Ala Ser Phe Asn Leu Val Gly Leu Phe Gly Thr Lys Thr Lys
         50                  55                  60

Ser Ser Asp Phe Asn Thr Ala Lys Leu Val Pro Asn Ile Ala Leu Asn
 65                  70                  75                  80

Arg Ala Val Val Glu Leu Tyr Thr Asp Thr Thr Phe Ala Trp Ser Val
                     85                  90                  95

Gly Ala Arg Ala
            100

<210> SEQ ID NO 66
<211> LENGTH: 100
<212> TYPE: PRT
<213> ORGANISM: Homo sapiens

<400> SEQUENCE: 66

Asn Val Ala Arg Pro Asn Pro Ala Tyr Gly Lys His Met Gln Asp Ala
  1               5                  10                  15

Glu Met Phe Thr Asn Ala Ala Tyr Met Ala Leu Ile Asn Trp Asp Arg
                 20                  25                  30

Phe Asp Val Phe Cys Thr Leu Gly Ala Thr Thr Gly Tyr Leu Lys Gly
             35                  40                  45

Asn Ser Ala Ser Phe Asn Leu Val Gly Leu Phe Gly Thr Lys Thr Gln
         50                  55                  60

Ser Thr Asn Phe Asn Thr Ala Lys Leu Val Pro Asn Thr Ala Leu Asn
 65                  70                  75                  80

Gln Ala Val Val Glu Leu Tyr Thr Asp Thr Thr Phe Ala Trp Ser Val
                     85                  90                  95

Gly Ala Arg Ala
            100

<210> SEQ ID NO 67
<211> LENGTH: 96
<212> TYPE: PRT
<213> ORGANISM: Homo sapiens

<400> SEQUENCE: 67

Ala Ser Arg Glu Asn Pro Ala Tyr Gly Lys His Met Gln Asp Ala Glu
  1               5                  10                  15
```

-continued

Met Phe Thr Asn Ala Ala Tyr Met Ala Leu Ile Asn Trp Asp Arg Phe
                20                  25                  30

Asp Val Phe Cys Thr Leu Gly Ala Thr Ser Gly Tyr Leu Lys Gly Asn
            35                  40                  45

Ser Ala Ala Phe Asn Leu Val Gly Leu Phe Gly Arg Asp Glu Thr Ala
        50                  55                  60

Val Ala Ala Asp Asp Ile Pro Asn Val Ser Leu Ser Gln Ala Val Val
65                  70                  75                  80

Glu Leu Tyr Thr Asp Thr Ala Phe Ala Trp Ser Val Gly Ala Arg Ala
                85                  90                  95

<210> SEQ ID NO 68
<211> LENGTH: 100
<212> TYPE: PRT
<213> ORGANISM: Homo sapiens

<400> SEQUENCE: 68

Tyr Thr Thr Ala Val Asp Arg Pro Asn Pro Ala Tyr Asn Lys His Leu
1               5                   10                  15

His Asp Ala Glu Trp Phe Thr Asn Ala Gly Ile Phe Ala Leu Ile Asn
                20                  25                  30

Trp Asp Arg Phe Asp Val Phe Cys Thr Leu Gly Ala Ser Asn Gly Ile
            35                  40                  45

Arg Lys Gly Asn Ser Thr Ala Phe Asn Leu Val Gly Leu Phe Gly Val
        50                  55                  60

Lys Gly Thr Thr Val Asn Ala Asn Glu Leu Pro Asn Val Ser Leu Ser
65                  70                  75                  80

Asn Gly Val Val Glu Leu Tyr Thr Asp Thr Ser Phe Ser Trp Ser Val
                85                  90                  95

Gly Ala Arg Ala
            100

<210> SEQ ID NO 69
<211> LENGTH: 100
<212> TYPE: PRT
<213> ORGANISM: Homo sapiens

<400> SEQUENCE: 69

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
                20                  25                  30

Ala Glu Phe Thr Ile Asn Lys Pro Lys Gly Tyr Val Gly Gln Glu Phe
            35                  40                  45

Pro Leu Asp Leu Lys Ala Gly Thr Asp Gly Val Thr Gly Thr Lys Asp
        50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 70
<211> LENGTH: 100
<212> TYPE: PRT
<213> ORGANISM: Homo sapiens

<400> SEQUENCE: 70

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Lys Glu Leu
        35                  40                  45

Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 71
<211> LENGTH: 100
<212> TYPE: PRT
<213> ORGANISM: Homo sapiens

<400> SEQUENCE: 71

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Lys Glu Phe
        35                  40                  45

Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 72
<211> LENGTH: 100
<212> TYPE: PRT
<213> ORGANISM: Homo sapiens

<400> SEQUENCE: 72

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Gln Glu Phe
        35                  40                  45

Pro Leu Ala Leu Ile Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 73
<211> LENGTH: 100
<212> TYPE: PRT
<213> ORGANISM: Homo sapiens

<400> SEQUENCE: 73

Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Lys Glu Phe
        35                  40                  45

Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 74
<211> LENGTH: 100
<212> TYPE: PRT
<213> ORGANISM: Homo sapiens

<400> SEQUENCE: 74

Ala Leu Trp Glu Cys Gly Cys Ala Thr Leu Gly Ala Ser Phe Gln Tyr
 1               5                  10                  15

Ala Gln Ser Lys Pro Lys Ile Glu Glu Leu Asn Val Leu Cys Asn Ala
            20                  25                  30

Ala Glu Phe Thr Ile Asn Lys Pro Lys Gly Tyr Val Gly Lys Glu Phe
        35                  40                  45

Pro Leu Asp Leu Thr Ala Gly Thr Asp Ala Ala Thr Gly Thr Lys Asp
    50                  55                  60

Ala Ser Ile Asp Tyr His Glu Trp Gln Ala Ser Leu Ser Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ser
            100

<210> SEQ ID NO 75
<211> LENGTH: 100
<212> TYPE: PRT
<213> ORGANISM: Homo sapiens

<400> SEQUENCE: 75

Ala Leu Trp Glu Cys Gly Cys Ala Thr Leu Gly Ala Ser Phe Gln Tyr
 1               5                  10                  15

Ala Gln Ser Lys Pro Lys Val Glu Glu Leu Asn Val Leu Cys Asn Ala
            20                  25                  30

Ser Glu Phe Thr Ile Asn Lys Pro Lys Gly Tyr Val Gly Ala Glu Phe
        35                  40                  45

Pro Leu Asn Ile Thr Ala Gly Thr Glu Ala Ala Thr Gly Thr Lys Asp

```
            50                  55                  60
Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100

<210> SEQ ID NO 76
<211> LENGTH: 100
<212> TYPE: PRT
<213> ORGANISM: Homo sapiens

<400> SEQUENCE: 76

Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
                 20                  25                  30

Ser Glu Phe Thr Ile Asn Lys Pro Lys Gly Tyr Val Gly Ala Glu Phe
            35                  40                  45

Pro Leu Asp Ile Thr Ala Gly Thr Glu Ala Ala Thr Gly Thr Lys Asp
 50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100

<210> SEQ ID NO 77
<211> LENGTH: 100
<212> TYPE: PRT
<213> ORGANISM: Homo sapiens

<400> SEQUENCE: 77

Ala Leu Trp Glu Cys Gly Cys Ala Thr Leu Gly Ala Ser Phe Gln Tyr
  1               5                  10                  15

Ala Gln Ser Lys Pro Lys Val Glu Glu Leu Asn Val Leu Cys Asn Ala
                 20                  25                  30

Ser Glu Phe Thr Ile Asn Lys Pro Lys Gly Tyr Val Gly Ala Glu Phe
            35                  40                  45

Pro Leu Asp Ile Thr Ala Gly Thr Glu Ala Ala Thr Gly Thr Lys Asp
 50                  55                  60

Ala Ser Ile Asp Tyr His Glu Trp Gln Ala Ser Leu Ala Leu Ser Tyr
 65                  70                  75                  80

Arg Leu Asn Met Phe Thr Pro Tyr Ile Gly Val Lys Trp Ser Arg Val
                 85                  90                  95

Ser Phe Asp Ala
            100

<210> SEQ ID NO 78
<211> LENGTH: 100
<212> TYPE: PRT
<213> ORGANISM: Homo sapiens

<400> SEQUENCE: 78

Ala Leu Trp Glu Cys Gly Cys Ala Thr Leu Gly Ala Ser Phe Gln Tyr
  1               5                  10                  15
```

Ala Gln Ser Lys Pro Lys Val Glu Glu Leu Asn Val Leu Cys Asp Ala
            20                  25                  30

Ser Glu Phe Thr Ile Asn Lys Pro Lys Gly Tyr Val Gly Ala Glu Phe
                35                  40                  45

Pro Leu Asp Ile Thr Ala Gly Thr Glu Ala Ala Thr Gly Thr Lys Asp
            50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Val
                85                  90                  95

Ser Phe Asp Ala
            100

<210> SEQ ID NO 79
<211> LENGTH: 100
<212> TYPE: PRT
<213> ORGANISM: Homo sapiens

<400> SEQUENCE: 79

Ala Leu Trp Glu Cys Gly Cys Ala Thr Leu Gly Ala Ser Phe Gln Tyr
1               5                   10                  15

Ala Gln Ser Lys Pro Lys Val Glu Glu Leu Asn Val Leu Cys Asn Ala
            20                  25                  30

Ala Glu Phe Thr Ile Asn Lys Pro Lys Gly Tyr Val Gly Gln Glu Phe
                35                  40                  45

Pro Leu Asn Ile Lys Ala Gly Thr Val Ser Ala Thr Asp Thr Lys Asp
            50                  55                  60

Ala Ser Ile Asp Tyr His Glu Trp Gln Ala Ser Leu Ala Leu Ser Tyr
65                  70                  75                  80

Arg Leu Asn Met Phe Thr Pro Tyr Ile Gly Val Lys Trp Ser Arg Ala
                85                  90                  95

Ser Phe Asp Ala
            100

<210> SEQ ID NO 80
<211> LENGTH: 100
<212> TYPE: PRT
<213> ORGANISM: Homo sapiens

<400> SEQUENCE: 80

Gly Leu Trp Glu Cys Gly Cys Ala Thr Leu Gly Glu Ser Phe Gln Tyr
1               5                   10                  15

Ala Gln Ser Lys Pro Lys Val Glu Glu Leu Asn Val Ile Cys Asn Val
            20                  25                  30

Ser Gln Phe Ser Val Asn Lys Pro Lys Gly Tyr Lys Gly Val Ala Phe
                35                  40                  45

Pro Leu Pro Thr Asp Ala Gly Val Ala Thr Ala Thr Gly Thr Lys Ser
            50                  55                  60

Ala Thr Ile Asn Tyr His Glu Trp Gln Val Gly Ala Ser Leu Ser Tyr
65                  70                  75                  80

Arg Leu Asn Ser Leu Val Pro Tyr Ile Gly Val Gln Trp Ser Arg Ala
                85                  90                  95

Thr Phe Asp Ala
            100

<210> SEQ ID NO 81

-continued

```
<211> LENGTH: 94
<212> TYPE: PRT
<213> ORGANISM: Homo sapiens

<400> SEQUENCE: 81

Asp Thr Ile Arg Ile Ala Gln Pro Lys Ser Ala Thr Thr Val Phe Asp
 1               5                  10                  15

Val Thr Thr Leu Asn Pro Thr Ile Ala Gly Ala Gly Asp Val Lys Ala
            20                  25                  30

Ser Ala Glu Gly Gln Leu Gly Asp Thr Met Gln Ile Val Ser Leu Gln
        35                  40                  45

Leu Asn Lys Met Lys Ser Arg Lys Ser Cys Gly Ile Ala Val Gly Thr
50                  55                  60

Thr Ile Val Asp Ala Asp Lys Tyr Ala Val Thr Val Glu Thr Arg Leu
65                  70                  75                  80

Ile Asp Glu Arg Ala Ala His Val Asn Ala Gln Phe Arg Phe
                85                  90

<210> SEQ ID NO 82
<211> LENGTH: 92
<212> TYPE: PRT
<213> ORGANISM: Homo sapiens

<400> SEQUENCE: 82

Asp Thr Ile Arg Ile Ala Gln Pro Lys Ser Ala Glu Thr Ile Phe Asp
 1               5                  10                  15

Val Thr Thr Leu Asn Pro Thr Ile Ala Gly Ala Gly Asp Val Lys Thr
            20                  25                  30

Ser Ala Glu Gly Gln Leu Gly Asp Thr Met Gln Ile Val Ser Leu Gln
        35                  40                  45

Leu Asn Met Lys Ser Arg Lys Cys Gly Ile Ala Val Gly Thr Thr Ile
50                  55                  60

Val Asp Ala Asp Lys Tyr Ala Ile Thr Val Glu Thr Arg Leu Ile Asp
65                  70                  75                  80

Glu Arg Ala Ala His Val Asn Ala Gln Phe Arg Phe
                85                  90

<210> SEQ ID NO 83
<211> LENGTH: 94
<212> TYPE: PRT
<213> ORGANISM: Homo sapiens

<400> SEQUENCE: 83

Asp Thr Ile Arg Ile Ala Gln Pro Lys Ser Ala Thr Ala Ile Phe Asp
 1               5                  10                  15

Thr Thr Thr Leu Asn Pro Thr Ile Ala Gly Ala Gly Asp Val Lys Thr
            20                  25                  30

Gly Thr Glu Gly Gln Leu Gly Asp Thr Met Gln Ile Val Ser Leu Gln
        35                  40                  45

Leu Asn Lys Met Lys Ser Arg Lys Ser Cys Gly Ile Ala Val Gly Thr
50                  55                  60

Thr Ile Val Asp Ala Asp Lys Tyr Ala Val Thr Val Glu Thr Arg Leu
65                  70                  75                  80

Ile Asp Glu Arg Ala Ala His Val Asn Ala Gln Phe Arg Phe
                85                  90

<210> SEQ ID NO 84
```

-continued

```
<211> LENGTH: 94
<212> TYPE: PRT
<213> ORGANISM: Homo sapiens

<400> SEQUENCE: 84

Asp Thr Ile Arg Ile Ala Gln Pro Lys Ser Ala Thr Ala Ile Phe Asp
  1               5                  10                  15

Thr Thr Thr Leu Asn Pro Thr Ile Ala Gly Ala Gly Asp Val Lys Ala
             20                  25                  30

Ser Ala Glu Gly Gln Leu Gly Asp Thr Met Gln Ile Val Ser Leu Gln
         35                  40                  45

Leu Asn Lys Met Lys Ser Arg Lys Ser Cys Gly Ile Ala Val Gly Thr
     50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90

<210> SEQ ID NO 85
<211> LENGTH: 94
<212> TYPE: PRT
<213> ORGANISM: Homo sapiens

<400> SEQUENCE: 85

Asp Thr Ile Arg Ile Ala Gln Pro Lys Leu Ala Thr Ala Ile Phe Asp
  1               5                  10                  15

Thr Thr Thr Leu Asn Pro Thr Ile Ala Gly Ala Gly Asp Glu Lys Ala
             20                  25                  30

Asn Ala Glu Gly Gln Leu Gly Asp Thr Met Gln Ile Val Ser Leu Gln
         35                  40                  45

Leu Asn Lys Met Lys Ser Arg Lys Ser Cys Gly Ile Ala Val Gly Thr
     50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90

<210> SEQ ID NO 86
<211> LENGTH: 95
<212> TYPE: PRT
<213> ORGANISM: Homo sapiens

<400> SEQUENCE: 86

Asp Thr Ile Arg Ile Ala Gln Pro Arg Leu Val Thr Pro Val Val Asp
  1               5                  10                  15

Ile Thr Thr Leu Asn Pro Thr Ile Ala Gly Ala Cys Asp Ser Lys Ala
             20                  25                  30

Gly Asn Thr Glu Gly Gln Ile Ser Asp Thr Met Gln Ile Val Ser Leu
         35                  40                  45

Gln Leu Asn Lys Met Lys Ser Arg Lys Ser Cys Gly Ile Ala Val Gly
     50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg Phe
                 85                  90                  95

<210> SEQ ID NO 87
<211> LENGTH: 95
```

```
<212> TYPE: PRT
<213> ORGANISM: Homo sapiens

<400> SEQUENCE: 87

Asp Thr Ile Arg Ile Ala Gln Pro Lys Leu Ala Glu Ala Ile Leu Asp
  1               5                  10                  15

Val Thr Thr Leu Asn Arg Thr Thr Ala Gly Lys Gly Ser Val Val Ser
             20                  25                  30

Ala Gly Thr Asp Asn Glu Leu Ala Asp Thr Met Gln Ile Val Ser Leu
         35                  40                  45

Gln Leu Asn Lys Met Lys Ser Arg Lys Ser Cys Gly Ile Ala Val Gly
     50                  55                  60

Thr Thr Ile Val Asp Ala Asp Lys Tyr Ala Val Thr Val Glu Ala Arg
 65                  70                  75                  80

Leu Ile Asp Glu Arg Ala Ala His Val Asn Ala Gln Phe Arg Phe
                 85                  90                  95

<210> SEQ ID NO 88
<211> LENGTH: 94
<212> TYPE: PRT
<213> ORGANISM: Homo sapiens

<400> SEQUENCE: 88

Asp Thr Ile Arg Ile Ala Gln Pro Lys Leu Ala Lys Pro Val Leu Asp
  1               5                  10                  15

Thr Thr Thr Leu Asn Pro Thr Ile Ala Gly Lys Gly Thr Val Val Ser
             20                  25                  30

Ser Ala Glu Asn Glu Leu Ala Asp Thr Met Gln Ile Val Ser Leu Gln
         35                  40                  45

Leu Asn Lys Met Lys Ser Arg Lys Ser Cys Gly Ile Ala Val Gly Thr
     50                  55                  60

Thr Ile Val Asp Ala Asp Lys Tyr Ala Val Thr Val Glu Thr Arg Leu
 65                  70                  75                  80

Ile Asp Glu Arg Ala Ala His Val Asn Ala Gln Phe Arg Phe
                 85                  90

<210> SEQ ID NO 89
<211> LENGTH: 94
<212> TYPE: PRT
<213> ORGANISM: Homo sapiens

<400> SEQUENCE: 89

Asp Thr Ile Arg Ile Ala Gln Pro Lys Leu Ala Glu Ala Ile Leu Asp
  1               5                  10                  15

Val Thr Thr Leu Asn Pro Thr Ile Ala Gly Lys Gly Thr Val Val Ala
             20                  25                  30

Ser Gly Ser Asp Asn Asp Leu Ala Asp Thr Met Gln Ile Val Ser Leu
         35                  40                  45

Gln Leu Asn Lys Met Lys Ser Arg Lys Ser Cys Gly Ile Ala Val Gly
     50                  55                  60

Thr Thr Ile Val Asp Ala Asp Lys Tyr Ala Val Thr Val Glu Thr Arg
 65                  70                  75                  80

Leu Ile Asp Glu Arg Ala Ala His Val Asn Ala Gln Phe Arg
                 85                  90

<210> SEQ ID NO 90
<211> LENGTH: 95
<212> TYPE: PRT
```

<213> ORGANISM: Homo sapiens

<400> SEQUENCE: 90

Asp Thr Ile Arg Ile Ala Gln Pro Lys Leu Ala Glu Ala Val Leu Asp
1               5                   10                  15
Val Thr Thr Leu Asn Pro Thr Ile Ala Gly Lys Gly Ser Val Val Ala
            20                  25                  30
Ser Gly Ser Glu Asn Glu Leu Ala Asp Thr Met Gln Ile Val Ser Leu
        35                  40                  45
Gln Leu Asn Lys Met Lys Ser Arg Lys Ser Cys Gly Ile Ala Val Gly
    50                  55                  60
Thr Thr Ile Val Asp Ala Asp Lys Tyr Ala Val Thr Val Glu Thr Arg
65                  70                  75                  80
Leu Ile Asp Glu Arg Ala Ala His Val Asn Ala Gln Phe Arg Phe
                85                  90                  95

<210> SEQ ID NO 91
<211> LENGTH: 91
<212> TYPE: PRT
<213> ORGANISM: Homo sapiens

<400> SEQUENCE: 91

Asp Thr Ile Arg Ile Ala Gln Pro Lys Leu Glu Thr Ser Ile Leu Lys
1               5                   10                  15
Met Thr Thr Trp Asn Pro Thr Ile Ser Gly Ser Gly Ile Asp Val Asp
            20                  25                  30
Thr Lys Ile Thr Asp Thr Leu Gln Ile Val Ser Leu Gln Leu Asn Lys
        35                  40                  45
Met Lys Ser Arg Lys Ser Cys Leu Ile Ala Ile Gly Thr Thr Ile Val
    50                  55                  60
Asp Ala Asp Lys Tyr Ala Val Thr Val Glu Thr Arg Leu Ile Asp Glu
65                  70                  75                  80
Arg Ala Ala His Val Asn Ala Gln Phe Arg Phe
                85                  90

<210> SEQ ID NO 92
<211> LENGTH: 93
<212> TYPE: PRT
<213> ORGANISM: Homo sapiens

<400> SEQUENCE: 92

Asp Asn Ile Arg Ile Ala Gln Pro Lys Leu Pro Thr Ala Val Leu Asn
1               5                   10                  15
Leu Thr Ala Trp Asn Pro Ser Leu Leu Gly Asn Ala Thr Ala Leu Ser
            20                  25                  30
Thr Thr Asp Ser Phe Ser Asp Phe Met Gln Ile Val Ser Cys Gln Ile
        35                  40                  45
Asn Lys Phe Lys Ser Arg Lys Ala Cys Val Thr Ala Val Ala Thr Leu
    50                  55                  60
Ile Val Asp Ala Asp Lys Trp Ser Leu Thr Ala Glu Ala Arg Leu Asn
65                  70                  75                  80
Asp Glu Arg Ala Ala His Ser Gly Ala Gln Phe Arg Phe
                85                  90

<210> SEQ ID NO 93
<211> LENGTH: 17
<212> TYPE: PRT
<213> ORGANISM: Homo sapiens

```
<400> SEQUENCE: 93

Cys Thr Gly Ser Ala Ala Ala Asn Tyr Thr Thr Ala Val Asp Arg Pro
 1               5                  10                  15
Asn

<210> SEQ ID NO 94
<211> LENGTH: 18
<212> TYPE: PRT
<213> ORGANISM: Homo sapiens

<400> SEQUENCE: 94

Cys Thr Gly Asp Ala Asp Leu Thr Thr Ala Pro Thr Pro Ala Ser Arg
 1               5                  10                  15
Glu Asn

<210> SEQ ID NO 95
<211> LENGTH: 19
<212> TYPE: PRT
<213> ORGANISM: Homo sapiens

<400> SEQUENCE: 95

Cys Thr Thr Ala Thr Gly Asn Ala Ala Ala Pro Ser Thr Cys Thr Ala
 1               5                  10                  15
Arg Glu Asn

<210> SEQ ID NO 96
<211> LENGTH: 17
<212> TYPE: PRT
<213> ORGANISM: Homo sapiens

<400> SEQUENCE: 96

Cys Ala Ser Gly Thr Ala Ser Asn Thr Thr Val Ala Ala Asp Arg Ser
 1               5                  10                  15
Asn

<210> SEQ ID NO 97
<211> LENGTH: 15
<212> TYPE: PRT
<213> ORGANISM: Homo sapiens

<400> SEQUENCE: 97

Cys Phe Gly Val Lys Gly Thr Thr Val Asn Ala Asn Glu Lys Pro
 1               5                  10                  15

<210> SEQ ID NO 98
<211> LENGTH: 15
<212> TYPE: PRT
<213> ORGANISM: Homo sapiens

<400> SEQUENCE: 98

Cys Phe Gly Arg Asp Glu Thr Ala Val Ala Ala Asp Asp Ile Pro
 1               5                  10                  15

<210> SEQ ID NO 99
<211> LENGTH: 18
<212> TYPE: PRT
<213> ORGANISM: Homo sapiens

<400> SEQUENCE: 99

Cys Phe Gly Asp Asn Glu Asn His Ala Thr Val Ser Asp Ser Lys Leu
 1               5                  10                  15
```

Val Pro

<210> SEQ ID NO 100
<211> LENGTH: 14
<212> TYPE: PRT
<213> ORGANISM: Homo sapiens

<400> SEQUENCE: 100

Cys Ile Gly Leu Ala Gly Thr Asp Phe Ala Asn Gln Arg Pro
1               5                   10

<210> SEQ ID NO 101
<211> LENGTH: 13
<212> TYPE: PRT
<213> ORGANISM: Homo sapiens

<400> SEQUENCE: 101

Cys Gln Ile Asn Lys Phe Lys Ser Arg Lys Ala Cys Gly
1               5                   10

<210> SEQ ID NO 102
<211> LENGTH: 13
<212> TYPE: PRT
<213> ORGANISM: Homo sapiens

<400> SEQUENCE: 102

Cys Gln Ile Asn Lys Met Lys Ser Arg Phe Ala Cys Gly
1               5                   10

<210> SEQ ID NO 103
<211> LENGTH: 13
<212> TYPE: PRT
<213> ORGANISM: Homo sapiens

<400> SEQUENCE: 103

Cys Gln Leu Asn Lys Met Lys Ser Arg Lys Ala Cys Gly
1               5                   10

<210> SEQ ID NO 104
<211> LENGTH: 13
<212> TYPE: PRT
<213> ORGANISM: Homo sapiens

<400> SEQUENCE: 104

Cys Gln Ile Asn Lys Phe Lys Ser Arg Phe Ala Cys Gly
1               5                   10

<210> SEQ ID NO 105
<211> LENGTH: 38
<212> TYPE: DNA
<213> ORGANISM: Homo sapiens

<400> SEQUENCE: 105
atgaaaaaac tcttaaagtc ggcgttatta tccgccgc                          38

<210> SEQ ID NO 106
<211> LENGTH: 44
<212> TYPE: DNA
<213> ORGANISM: Homo sapiens

<400> SEQUENCE: 106
atgaaaaaac tcttgaaatc ggtattagtg tttgccgctt tgag                   44

```
<210> SEQ ID NO 107
<211> LENGTH: 44
<212> TYPE: DNA
<213> ORGANISM: Homo sapiens

<400> SEQUENCE: 107
atgaaaaaac tcttaaaatc ggcattatta tttgccgctg cggg          44

<210> SEQ ID NO 108
<211> LENGTH: 44
<212> TYPE: DNA
<213> ORGANISM: Homo sapiens

<400> SEQUENCE: 108
atgaaaaaac tcttgaaatc ggcattattg tttgccgcta cggg          44

<210> SEQ ID NO 109
<211> LENGTH: 50
<212> TYPE: DNA
<213> ORGANISM: Homo sapiens

<400> SEQUENCE: 109
atgaaaaaac tcttgaaatc ggtattagca tttgccgttt tgggttctgc    50

<210> SEQ ID NO 110
<211> LENGTH: 40
<212> TYPE: DNA
<213> ORGANISM: Homo sapiens

<400> SEQUENCE: 110
ttagaatctg aactgaccag atacgtgagc agctctctcg               40

<210> SEQ ID NO 111
<211> LENGTH: 35
<212> TYPE: DNA
<213> ORGANISM: Homo sapiens

<400> SEQUENCE: 111
ttagaagcgg aattgtgcat ttacgtgagc agctc                    35

<210> SEQ ID NO 112
<211> LENGTH: 43
<212> TYPE: DNA
<213> ORGANISM: Homo sapiens

<400> SEQUENCE: 112
ttagaatctg aattgagcat taatgtgagc agctctttcg tcg           43

<210> SEQ ID NO 113
<211> LENGTH: 51
<212> TYPE: DNA
<213> ORGANISM: Homo sapiens

<400> SEQUENCE: 113
ttagaatctg aattgaccat tcatgtgagc agctctttca ttgattaagc g  51

<210> SEQ ID NO 114
<211> LENGTH: 42
<212> TYPE: DNA
<213> ORGANISM: Homo sapiens

<400> SEQUENCE: 114
ttagaaacgg aactgagcat ttacgtgagc tgctctttca tc            42
```